United States Patent
Hu et al.

(10) Patent No.: US 8,821,408 B2
(45) Date of Patent: Sep. 2, 2014

(54) DATA MINING SYSTEM FOR NONINVASIVE INTRACRANIAL PRESSURE ASSESSMENT

(75) Inventors: Xiao Hu, Los Angeles, CA (US); Valeriy I. Nenov, Westchester, CA (US); Neil A. Martin, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 1484 days.

(21) Appl. No.: 12/296,087

(22) PCT Filed: Apr. 5, 2007

(86) PCT No.: PCT/US2007/008534
§ 371 (c)(1),
(2), (4) Date: Oct. 5, 2009

(87) PCT Pub. No.: WO2007/117570
PCT Pub. Date: Oct. 18, 2007

(65) Prior Publication Data
US 2010/0049082 A1  Feb. 25, 2010

Related U.S. Application Data

(60) Provisional application No. 60/789,410, filed on Apr. 5, 2006.

(51) Int. Cl.
*A61B 5/00* (2006.01)
*A61B 5/03* (2006.01)
*G05B 13/02* (2006.01)

(52) U.S. Cl.
USPC ........... 600/561; 600/300; 600/301; 600/438; 600/587; 700/29

(58) Field of Classification Search
USPC ............ 600/300, 301, 438, 561, 587; 700/29
See application file for complete search history.

(56) References Cited

U.S. PATENT DOCUMENTS

| | | | | |
|---|---|---|---|---|
| 4,971,061 A * | 11/1990 | Kageyama et al. | ........... | 600/438 |
| 6,248,080 B1 | 6/2001 | Miesel et al. | | |
| 6,875,176 B2 * | 4/2005 | Mourad et al. | ................ | 600/442 |
| 6,917,845 B2 * | 7/2005 | Hsiung et al. | ................ | 700/104 |
| 7,122,007 B2 * | 10/2006 | Querfurth | ..................... | 600/485 |
| 7,547,283 B2 * | 6/2009 | Mourad et al. | ................ | 600/459 |
| 7,815,574 B2 * | 10/2010 | Mourad et al. | ................ | 600/453 |
| 8,057,679 B2 * | 11/2011 | Yu et al. | ........................ | 210/645 |
| 2002/0082514 A1 | 6/2002 | Williams et al. | | |

(Continued)

OTHER PUBLICATIONS

Andersson, "Adaptive forgetting in recursive identification through multiple models," Int. J Control, 1985, vol. 42, No. 5, 1175-1193.

(Continued)

*Primary Examiner* — Sean Dougherty
(74) *Attorney, Agent, or Firm* — James W. Hill; John P. O'Banion

(57) ABSTRACT

Systems and methods are described for noninvasively assessing an intracranial pressure of a patient. Some embodiments include providing a simulation model with a measured arterial blood pressure of the patient. Some embodiments further include providing the simulation model with a measured cerebral blood flow velocity of the patient. The simulation model correlates arterial blood pressure values, cerebral blood flow velocity values, and intracranial pressure values. Some embodiments further includes determining an intracranial pressure of the patient based on the simulation model. Some embodiments further includes creating an output data set indicative of the determined intracranial pressure.

46 Claims, 12 Drawing Sheets

(56) References Cited

U.S. PATENT DOCUMENTS

| | | | |
|---|---|---|---|
| 2002/0095087 A1* | 7/2002 | Mourad et al. | 600/442 |
| 2003/0088320 A1* | 5/2003 | Sale | 700/30 |
| 2003/0191409 A1* | 10/2003 | Yost et al. | 600/561 |
| 2003/0199784 A1* | 10/2003 | Lenhardt | 600/561 |
| 2004/0049105 A1* | 3/2004 | Crutchfield et al. | 600/407 |
| 2004/0073453 A1 | 4/2004 | Nenov et al. | |
| 2004/0087863 A1* | 5/2004 | Eide | 600/500 |
| 2005/0015009 A1* | 1/2005 | Mourad et al. | 600/438 |
| 2005/0216114 A1* | 9/2005 | Hsiung et al. | 700/108 |
| 2006/0079773 A1* | 4/2006 | Mourad et al. | 600/438 |
| 2007/0016031 A1* | 1/2007 | Mourad et al. | 600/437 |
| 2007/0123796 A1* | 5/2007 | Lenhardt et al. | 600/561 |
| 2007/0219645 A1* | 9/2007 | Thomas et al. | 700/29 |

OTHER PUBLICATIONS

Hu, et al., "A Data mining framework of noninvasive intracranial pressure assessment," Biomedical Signal Processing and Control 1 (2006) 64-77.

Aaslid, et al., "Noninvasive transcranial Doppler ultrasound recording of flow velocity in basal cerebral arteries," J Neurosurg, vol. 57, No. 6, pp. 769-774, 1982.

Claude, et al., "Fetal Bran MRI: Segmentation and Biometric Analysis of the Posterior Fossa," IEEE Transactions on Biomedical Engineering, vol. 51 No. 4, Apr. 2004 617-626.

Corno, et al., "A Mathematical Model of Neonatal Tidal Liquid Ventilation Integrating Airway Mechanics and Gas Transfer Phenomena," IEEE Transactions on Biomedical Engineering, vol. 51 No. 4, Apr. 2004 604-611.

Czosnyka, et al., "Continuous Assessment of the cerebral vasomotor reactivity in head injury," Neurosurgery 41 (1) (1997) 11-17 (discussion 17-9).

Czosnyka, et al., "Monitoring of cerebral autoregulation in head-injured patients," Stroke 27 (10) (1996) 1829-1834.

Hu, et al., "Estimation of Hidden State Variables of the Intracranial System Using Constrained Nonlinear Kalman Filters," IEEE Transactions on Biomedical Engineering, vol. 54, No. 4, Apr. 2007 597-610.

Hu, et al., "Integrative Analysis of Intracranial Pressure and R-R Interval Signals: a Study of ICP B-Wave using Casual Coherence, "Proceedings of the 28th IEEE EMBS Annual International Conference, New York (2006).

Hu, et al., "Multivariate AR modeling of electromyography for the classification of upper arm movements," Clin. Neurophysiol. 115 (6) (2004) 1276-1287.

Hu, et al., "Nonlinear analysis of cerebral hemodynamic and intracranial pressure signals for characterization of autoregulation," IEEE Transactions on Biomedical Engineering, vol. 53: No. 2, Feb. 2006, 195-209.

Martinez, et al., "A Wavelet-Based ECG Delineator: Evaluation on Standard Databases," IEEE Transactions on Biomedical Engineering, vol. 51 No. 4, Apr. 2004 570-581.

Moxon, et al., "Ceramic-Based Multisite Electrode Arrays for Chronic Single-Neuron Recording," IEEE Transactions on Biomedical Engineering, vol. 51 No. 4, Apr. 2004 647-656.

Nishizawa, et al., "Numerical Study on an Equivalent Source Model for Inhomogeneous Magnetic Field Dosimetry in the Low-Frequency Range," IEEE Transactions on Biomedical Engineering, vol. 51 No. 4, Apr. 2004 612-616.

Osowski, et al., "Support Vector Machine-Based Expert System for Reliable Heartbeat Recognition," IEEE Transactions on Biomedical Engineering, vol. 51 No. 4, Apr. 2004 582-589.

Overschee, et al., "Subspace Identification for Linear Systems: Theory, Implementation, Applications," Kluwer Academic Publishers, Boston, 1996.

Patton, et al., "Robot-Assisted Adaptive Training: Custom Force Fields for Teaching Movement Patterns," IEEE Transactions on Biomedical Engineering, vol. 51 No. 4, Apr. 2004 636-646.

Schimpf, et al., "Ellipsoidal Refinement of the Regularized Inverse: Performance in an Anatomically Realistic EEG Model," IEEE Transactions on Biomedical Engineering, vol. 51 No. 4, Apr. 2004 679-683.

Schmidt, et al., "Adaptive noninvasive assessment of intracranial pressure and cerebral autoregulation," Stroke 2003; 34: 84-89.

Schmidt, et al., "Evaluation of a method for noninvasive intracranial pressure assessment during infusion studies in patients with hydrocephalus," J Neurosurg 2000; 92: 793-800.

Schmidt, et al., "Noninvasive prediction of intracranial pressure curves using transcranial Doppler ultrasonography and blood pressure curves," Stroke 1997; 28: 2465-2472.

Schmidt, et al., "Preliminary experience of the estimation of cerebral perfusion pressure using transcranial Doppler ultrasonography," J Neurol Neurosurg Psychiatry 2001; 70: 198-204.

Schreiber, et al., "Improving Calibration of 3-D Video Oculography Systems," IEEE Transactions on Biomedical Engineering, vol. 51 No. 4, Apr. 2004 676-679.

Thong, et al., "Paroxysmal Atrial Fibrillation Prediction Using Isolated Premature Atrial Events and Paroxysmal Atrial Tachycardia," Proceedings of the 25th Annual International Conference of the IEEE EMBS, Cancun, Mexico (2003) 163-166.

Voskerician, et al., "In Vivo Inflammatory and Wound Healing Effects of Gold Electrode Volammetry for MEMS Micro-Reservoir Drug Delivery Device," IEEE Transactions on Biomedical Engineering, vol. 51 No. 4, Apr. 2004 627-635.

Xu, et al., "Predicting the Threshold of Pulse-Train Electrical Stimuli Using a Stochastic Auditory Nerve Model: The Effects of Stimulus Noise," IEEE Transactions on Biomedical Engineering, vol. 51 No. 4, Apr. 2004 590-603.

Zaghloul, et al., "Optic Nerve Signals in a Neuromorphic Chip I: Outer and Inner Retina Models," IEEE Transactions on Biomedical Engineering, vol. 51 No. 4, Apr. 2004 657-666.

Zaghloul, et al., "Optic Nerve Signals in a Neuromorphic Chip II: Testing and Results," IEEE Transactions on Biomedical Engineering, vol. 51 No. 4, Apr. 2004 667-675.

Poon, et al., "Cerebral blood flow (CBF)-directed management of ventilated head-injured patients," Acta Neurochir (2005) [Suppl] 95: 9-11.

Kirkness, et al., "Relationship of cerebral perfusion pressure levels to outcome in traumatic brain injury," Acta Neurochir (2005) [Suppl] 95: 13-16.

Steiner, et al, "Effects of moderate hyperventilation on cerebrovascular pressure-reactivity after head injury," Acta Neurochir (2005) [Suppl] 95: 17-20.

Chambers, et al., "Which paediatric head injured patients might benefit from decompression? Thresh9olds of ICP and CPP in the first six hours," Acta Neurochir (2005) [Suppl] 95: 21-21.

Balestreri, et al., "Association between outcome, cerebral pressure reactivity and slow ICP waves following head injury," Acta Neurochir (2005) [Suppl] 95: 25-28.

Jones, et al., "Quantification of secondary CPP insult severity in paediatric head injured patients using a pressure-time index," Acta Neurochir (2005) [Suppl] 95: 29-32.

Nilsson, et al., "The BrainIT Group: concept and current status 2004," Acta Neurochir (2005) [Suppl] 95: 33-37.

Barnes, et al., "Accurate data collection for head injury monitoring studies: a data validation methodology," Acta Neurochir (2005) [Suppl] 95: 39-41.

Smielewski, et al., "ICM+: software for on-line analysis of bedside monitoring data after severe head trauma," Acta Neurochir (2005) [Suppl] 95: 43-49.

Nilsson, et al., "Survey of traumatic brain injury management in European Brain-IT centres year 2001," Acta Neurochir (2005) [Suppl] 95: 51-53.

Meier, et al., "The importance of major extracranial injuries by the decompressive craniectomy in s4ever head injuries," Acta Neurochir (2005) [Suppl] 95: 55-57.

(56) References Cited

OTHER PUBLICATIONS

Wong, et al., "Beneficial effect of cerebrolysin on moderate and sever head injury patients: result of a cohort study," Acta Neurochir (2005) [Suppl] 95: 59-60.

Chan, et al., "Re-defining the ischemic threshold for jugular venous oxygen saturation—a microdialysis study in patients with severe head injury," Acta Neurochir (2005) [Suppl] 95: 63-66.

Chieregato, et al., "Estimated cerebral respiratory quotient and arteriovenous differences of CO2 in the ultra early detection of global ischemia in severe head injury," Acta Neurochir (2005) [Suppl] 95: 67-71.

Chan, et al., "Effect of ischemic preconditioning on brain tissue gases and pH during temporary cerebral artery occlusion," Acta Neurochir (2005) [Suppl] 95: 93-96.

Sarrafzadeh, et al., "Cerebral metabolism and intracranial hypertension in high grade aneurysmal subarachnoid haemorrhage patients," Acta Neurochir (2005) [Suppl] 95: 89-92.

Kett-White, et al., "Extracellular amino acid changes in patients during reversible cerebral ischemia," Acta Neurochir (2005) [Suppl] 95: 83-88.

Jaeger, et al., "Brain tissue oxygen (PtiO2): a clinical comparison of two monitoring devices," Acta Neurochir (2005) [Suppl] 95: 79-81.

Gasco, et al., "Linear correlation between stable intracranial pressure decrease and regional cerebral oxygenation improvement following mannitol administration in severe acute head injury patients," Acta Neurochir (2005) [Suppl] 95: 73-77.

Marmarou, "The importance of translational reasearch in brain injury," Acta Neurochir (2005) [Suppl] 95: 3-5.

\* cited by examiner

Table 1
Key Patient Characteristics

| | A | G | D | GCS | GOS_3 | GOS_12 | PID | ABP | CBFV | ICP |
|---|---|---|---|---|---|---|---|---|---|---|
| 1 | 58 | M | Left frontal SDH | 8 | 3 | 6 | 3 | 101.2 ± 22.8 | 77.1 ± 20.0 | 12.5 ± 2.3 |
| 2 | 57 | F | Left frontal SAH | 6 | 3 | 3 | 1 | 126.1 ± 38.5 | 132.6 ± 49.6 | 12.9 ± 3.7 |
| 3 | 68 | M | Brain Stem injury | 4 | Dead | | 3 | 92.3 ± 23.2 | 50.7 ± 14.3 | 23.5 ± 5.7 |
| 4 | 59 | F | Left frontal contusions | 8 | 3 | 5 | 6 | 132.8 ± 35.6 | 71.0 ± 20.4 | 15.3 ± 4.3 |
| 5 | 25 | M | SAH | 6 | 3 | 5 | 1 | 117.1 ± 17.9 | 27.8 ± 5.8 | 15.1 ± 3.9 |
| 6 | 29 | M | SAH in left sylvian fissure | 3 | 8 | 7 | 1 | 92.3 ± 19.8 | 42.8 ± 22.1 | 24.3 ± 5.3 |
| 7 | 47 | M | Bilateral frontal IAH | 7 | 3 | 3 | 1 | 81.7 ± 20.1 | 54.0 ± 17.3 | 8.8 ± 4.1 |
| 8 | 21 | M | Basal ganglia punctate hemorrhage | 7 | 3 | 3 | 3 | 132.6 ± 25.0 | 94.1 ± 15.1 | 11.7 ± 0.2 |
| 9 | | | | | | | | 74.8 ± 22.1 | 29.1 ± 19.0 | 9.6 ± 0.3 |

A: Age in years at injury.
G: Gender.
D: Diagnostic description.
GCS: Glasgow Coma Scale at measurement [44].
$GOSE_3$ : Three month Glasgow Outcome Score extended [45].
$GOSE_{12}$: Twelve month Glasgow Outcome Score extended.
PID: Post injury day at measurement.
ABP: Arterial blood pressure (mmHg).
CBFV: Cerebral blood flow velocity at MCA (cm/s).
ICP: Intracranial pressure (mmHg).
SAH: Subarachnoid hemorrhage.
SDH: Subdural hematoma.
IAH: Intracerebral hemorrhage.

DATA MINING SYSTEM FOR NONINVASIVE INTRACRANIAL PRESSURE ASSESSMENT

CROSS REFERENCE TO RELATED APPLICATIONS

This application claims the benefit under 35 U.S.C. §371 of International Patent Application No. PCT/US2007/008534, filed on Apr. 5, 2007, and titled "DATA MINING SYSTEM FOR NONINVASIVE INTRACRANIAL PRESSURE ASSESSMENT," which claims the benefit under 35 U.S.C. §119(e) of U.S. Provisional Patent Application No. 60/789,410, filed on Apr. 5, 2006, and titled "DATA MINING FRAMEWORK OF NONINVASIVE INTRACRANIAL PRESSURE," the entirety of which is hereby incorporated by reference.

GOVERNMENT LICENSE RIGHTS

This invention was made with Government support of Grant No. NS040122 awarded by the National Institutes of Health. The Government has certain rights in this invention.

BACKGROUND OF THE INVENTION

1. Field of the Invention

This disclosure relates to methods and apparatus for processing physiological information. The disclosure relates in particular to a methods and apparatus for the assessment and processing of intracranial pressure data.

2. Description of the Related Art

Although several noninvasive techniques of measuring intracranial pressure (ICP) have been proposed during the last decade, the only established means of ICP measurement is an invasive direct procedure, which accesses the intracranial space in ventricles, parenchymal, or epidural space for sensing ICP. Albeit this invasiveness, long term monitoring of ICP has been part of the established protocols of managing brain injury patients in a neurosurgical intensive care unit. The risk involved in an invasive ICP measurement is justified in such a critical scenario because of the demonstrated benefits of outcome improvement of brain injury patients. However, there are many other situations where an assessment of ICP, or even a monitoring, is desirable but an invasive procedure is inappropriate. For example, these situations may include: management of fulminant hepatic failure (FHF) and liver transplant patients where ICP monitoring allows a specific therapy to control intracranial hypertension but is especially risky for patients with coagulopathy; in a non-specialized units where the ICP sensor placement is not possible; and management of normal, pregnant women or those with pre-eclampsia. Furthermore, even in a neurosurgical setting, noninvasive ICP is a highly desirable follow-up assessment of hydrocephalous patients with implanted shunts.

Noninvasive assessment of ICP (NICP) has been pursued with several approaches that are based on different physical principles. Unfortunately, none of them has been clinically accepted. The existing approaches share the common idea of measuring an alternative physical variable that carries ICP information for its estimation. The relationship between ICP and these secondary measurements is governed by complex physical and physiological principles. Realistic mathematical expression of these principles are almost impossible or only available in a highly simplified form such that a straightforward formula cannot be established for representing such a relationship. Instead, advanced signal processing techniques are well justified in order to establish such hidden relationship between ICP and its secondary variables. The noninvasive ICP methods lack such built-in signal processing approaches.

SUMMARY OF THE INVENTION

In certain embodiments, a system for data mining cerebral hemodynamic signals for NICP assessment is disclosed. The system comprises two processes: a training process and a simulation process. In certain embodiments, the training process is used to explore existing information in the signal database and organize it into a mapping function by which the database becomes searchable. In certain embodiments, the simulation process constructs a hemodynamic feature vector from ABP and CBFV that can be used as the input to the mapping function for querying the database. The query will return the most suitable record that can be used for building an ICP estimation model on the fly. The simulation process then simulates this model to obtain the unobserved ICP.

In some embodiments, a system, for determining an estimated ICP of a first patient, is described that includes a processing module that receives a first input based on a first plurality of measurements of a first physiological parameter of the first patient, the first physiological parameter correlating with ICP, that receives a second input based on a second plurality of measurements of a second physiological parameter of the first patient, the second physiological parameter correlating with ICP, that processes the first and second inputs based on an ICP model, and that produces an output indicative of the estimated ICP of the first patient. The ICP model is preferably chosen from a plurality of potential ICP models, each of the potential ICP models having an associated mapping function that maps values of the first and second physiological parameters to at least one dissimilarity value, each of the at least one dissimilarity values representing a dissimilarity between an estimated ICP value or function and an observed ICP value or function.

In some embodiments, a hemodynamic feature vector includes values of, or derived from, the first and second physiological parameters discuss above. In some embodiments, the ICP model is chosen based on the dissimilarity values obtained by inputting data indicative the first patient's first plurality of measurements and second plurality of measurements into the mapping functions of each of the potential ICP models, based on the inputted data, outputting a corresponding dissimilarity value for each of the potential ICP models, and choosing an optimal dissimilarity value from among the corresponding dissimilarity values, based on at least on criterion. In some embodiments, each of the corresponding dissimilarity values comprise a scalar value. In some embodiments, the small the scalar value, the more similar the estimated ICP is to the measured ICP, and dissimilarity values can be comparable under the same criterion. In some embodiments, a hemodynamic feature vector includes derived values from the first patient's first plurality of measurements and second plurality of measurements. In some embodiments, the criterion is determining a minimum dissimilarity value or a maximum-score dissimilarity. In some embodiments, the dissimilarity value includes an expression of a cross correlation coefficient between estimated and observed ICP values or vectors, a pulsatile component of at least one of said first plurality of measurements and said second plurality of measurements, or a slow wave component of at least one of said first plurality of measurements and said second plurality of measurements.

In some embodiments, the system includes an output module that receives the output produced by the processing module. The output module can be an electronic display, a printed display, an audible display, or any other visual, audible, or tactile indication. In some embodiments, the processing module includes computer-executable instructions. The system can also include a storage module that stores data indicative of at least one of said first plurality of measurements and said second plurality of measurements. In some embodiments, the output includes data configured to be stored on a computer-readable medium. In some embodiments, at least one of the first and second physiological parameters include $pCO_2$, $pO_2$, arterial blood pressure, cerebral blood flow velocity, or an echocardiographic measurement. Additionally, the observed ICP value or function is preferably obtained from a patient other than said first patient.

Some embodiments described herein provide methods of determining an estimated ICP of a first patient. These methods preferably include inputting into an ICP model a first plurality of measurements, of a first physiological parameter of the first patient, the first physiological parameter correlating with ICP; inputting into an ICP model a second plurality of measurements, of a second physiological parameter of the first patient, the second physiological parameter correlating with ICP; and outputting from the ICP model the estimated ICP of the patient. The ICP model is preferably chosen from a plurality of potential ICP models, each of the potential ICP models having an associated mapping function that maps values of said first and second physiological parameters to at least one dissimilarity value, each of said at least one dissimilarity values representing a dissimilarity between an estimated ICP value or function and an observed ICP value or function.

In some embodiments, a hemodynamic feature vector includes the values of, or derived values from, the first and second physiological parameters. In some embodiments, the method also includes inputting the first patient's first plurality of measurements and second plurality of measurements into the mapping functions of each of the potential ICP models, outputting a corresponding dissimilarity value for each of the potential ICP models, and choosing an optimal dissimilarity value from among the corresponding dissimilarity values, based on at least one criterion.

In some embodiments, at least one criterion includes determining a minimum dissimilarity value or a maximum-score dissimilarity value from among the corresponding dissimilarity values. In some embodiments, the dissimilarity value includes an expression of a cross correlation coefficient between estimated and observed ICP values or vectors, a pulsatile component of at least one of said first plurality of measurements and said second plurality of measurements, or a slow wave component of at least one of said first plurality of measurements and said second plurality of measurements.

In some embodiments, a hemodynamic feature vector comprises derived values from the first patient's said first plurality of measurements and second plurality of measurements, and each of the corresponding dissimilarity values can comprise a scalar value. In some embodiments, the first plurality of measurements is obtained over time and said second plurality of measurements is obtained over time. The first and second physiological parameters can include $pCO_2$, arterial $pO_2$, arterial blood pressure, cerebral blood flow velocity, or an echocardiographic measurement. In some embodiments, the observed ICP values are obtained from a patient other than said first patient. And in some embodiments, a signal (e.g., an electrical signal) can include at least one of the first plurality of measurements and the second plurality of measurements.

Some embodiments disclosed herein relate to a system, for determining an estimated value or function of a first physiological parameter of a first patient. The system can include a processing module that (i) receives a first input based on a first plurality of measurements of a second physiological parameter of the first patient, the second physiological parameter correlating with the first physiological parameter; (ii) receives a second input based on a second plurality of measurements of a third physiological parameter of the first patient, the third physiological parameter correlating with the first physiological parameter; (iii) processes the first and second inputs based on a physiological-parameter model; and (iv) outputs data indicative of the estimated first physiological parameter of the first patient. The physiological-parameter model is preferably chosen from a plurality of potential physiological-parameter models, each of the potential physiological-parameter models having an associated mapping function that maps values of said second and third physiological parameters to at least one dissimilarity value, each of said at least one dissimilarity value representing a dissimilarity between an estimated first-physiological-parameter value or function and an observed first-physiological-parameter value or function.

In some embodiments, the first physiological parameter comprises intracranial pressure (ICP), and is some embodiments the second physiological parameter includes cerebral blood flow velocity (CBFV) and the third physiological parameter includes an arterial blood pressure (ABP). The first physiological parameter can also include cerebral blood flow velocity (CBFV), and the second physiological parameter can include intracranial pressure (ICP) and the third physiological parameter can include an arterial blood pressure (ABP).

In some embodiments, a method, of determining an estimated value or function of a first physiological parameter of a first patient, is described. The method preferably includes inputting into a physiological-parameter model a first plurality of measurements, of a second physiological parameter of the first patient, the second physiological parameter correlating with the first physiological parameter; inputting into the physiological-parameter model a second plurality of measurements, of a third physiological parameter of the first patient, the third physiological parameter correlating with the first physiological parameter; and outputting from the physiological-parameter model the estimated value or function of a first physiological parameter of the patient. The physiological-parameter model is preferably chosen from a plurality of potential physiological-parameter models, each of the potential physiological-parameter models having an associated mapping function that maps values of said second and third physiological parameters to at least one dissimilarity value, each of said at least one dissimilarity value representing a dissimilarity between an estimated first-physiological-parameter value or function and an observed first-physiological-parameter value or function.

In some embodiments, the first physiological parameter includes intracranial pressure (ICP), the second physiological parameter includes cerebral blood flow velocity (CBFV), and the third physiological parameter includes an arterial blood pressure (ABP). In some embodiments, the first physiological parameter includes cerebral blood flow velocity (CBFV), the second physiological parameter includes intracranial pressure (ICP), and the third physiological parameter includes an arterial blood pressure (ABP).

In certain embodiments, at least one of the arterial blood pressure values, the cerebral blood flow velocity values, and the intracranial pressure values is extracted from biological signal data by obtaining data on at least one of slow wave components, waveform analysis, and full dynamics. In certain embodiments, the at least one of the arterial blood pressure values, the cerebral blood flow velocity values, and the intracranial pressure values is extracted as a hemodynamic feature vector. In certain embodiments, the method further comprises organizing a database comprising second arterial blood pressure values, second cerebral blood flow velocity values, and second intracranial pressure values using a mapping function, and generating the simulation model using at least one of the second arterial blood pressure values, the second cerebral blood flow velocity values, and the second intracranial pressure values from the database. In certain embodiments, the mapping function outputs at least one dissimilarity measure. In certain embodiments, the database comprises at least one entry, and wherein the at least one entry is associated with at least one mapping function. In certain embodiments, the method further comprises providing a hemodynamic feature vector to a mapping function for querying the database, wherein the hemodynamic feature vector is generated from the arterial blood pressure values, the cerebral blood flow velocity values, and the intracranial pressure values, receiving a record from the database that is configured to generate the simulation model, and generating the simulation model to obtain an unobserved ICP.

In certain embodiments, a system, for noninvasively assessing an intracranial pressure of a patient, is disclosed. The system comprises a storage module configured to store a measured first arterial blood pressure of the patient and a measured first cerebral blood flow velocity of the patient. The system further comprises a database module configured to store arterial blood pressure values, cerebral blood flow velocity values, and intracranial pressure values. The system further comprises a processor module configured to generate a simulation model for determining intracranial pressure values of the patient using the patient's measured arterial blood pressure, the patient's measured cerebral blood flow, the arterial blood pressure values, the cerebral blood flow velocity values, and the intracranial pressure values. The system further comprises an output module configured to output a data set indicative of an intracranial pressure value of the patient determined by the simulation model.

In certain embodiments, the system further comprises an extraction module configured to extract a hemodynamic feature vector from the first arterial blood pressure values, the first cerebral blood flow velocity values, and the first intracranial pressure values.

In certain embodiments, a system, for noninvasively assessing an intracranial pressure of a patient, is disclosed. The system comprises means for providing to a simulation model a measured arterial blood pressure of the patient and a measured cerebral blood flow velocity of the patient, wherein the simulation model correlates arterial blood pressure values, cerebral blood flow velocity values, and intracranial pressure values. The system further comprises means for determining an intracranial pressure of the patient based on the simulation model. The system further comprises means for creating an output data set indicative of the determined intracranial pressure.

For purposes of summarizing this disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

FIG. 4 illustrates key characteristics of nine patients used in the implementation according to one embodiment.

DETAILED DESCRIPTION OF EXEMPLARY EMBODIMENTS

Figure 1:
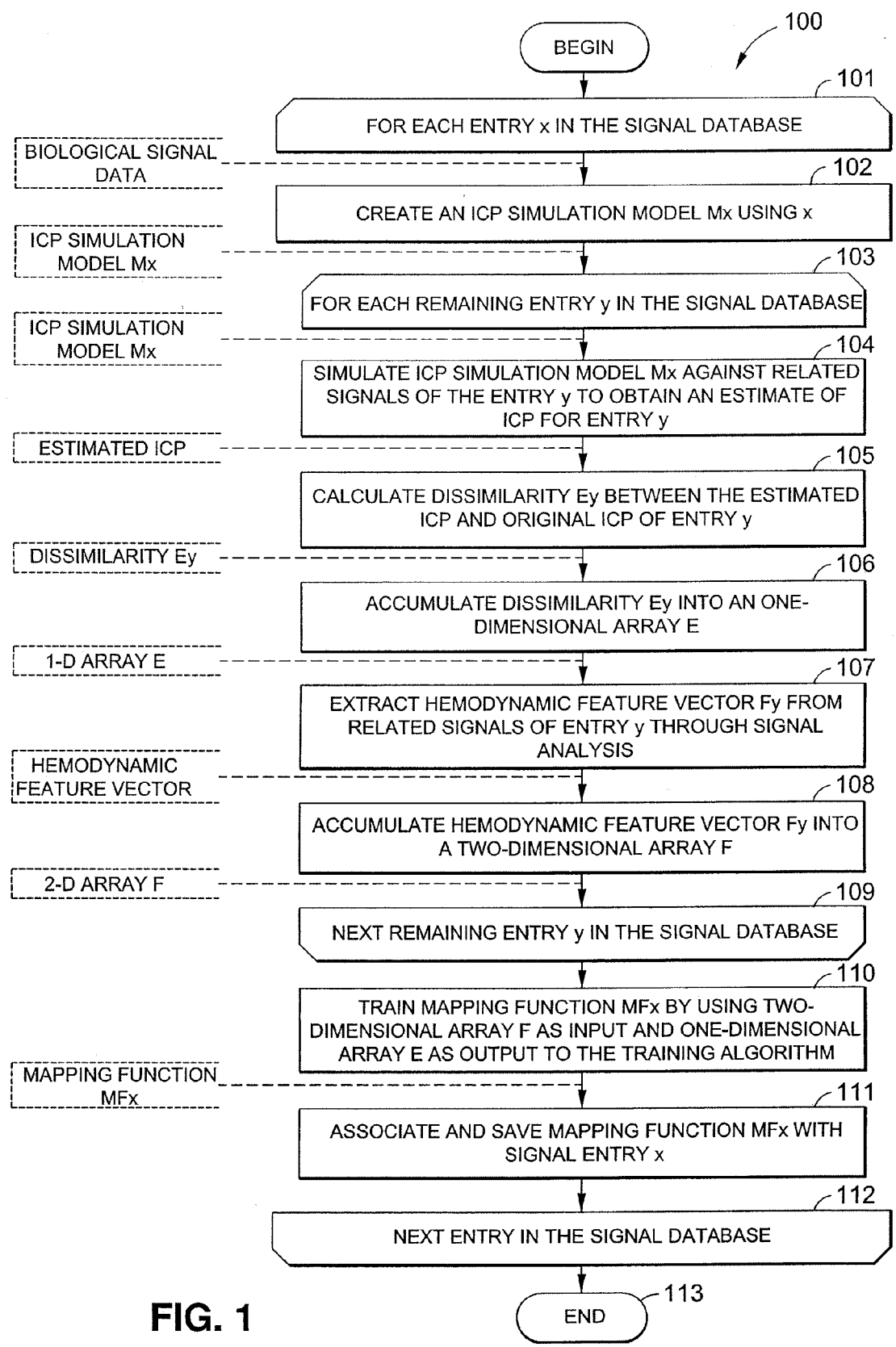
FIG. 1 illustrates a diagram of a training process of the noninvasive intracranial pressure estimation system according to certain embodiments.

In certain embodiments, a system for simulating ICP using various biological signal data is proposed. In some embodiments, biological signal data such as continuous arterial blood pressure (ABP) cerebral blood flow velocity (CBFV), and observed ICP may be used to simulate unobserved ICP. This simulation may be supplemented by using data on hemodynamic features extracted from measured ABP and CBFV. In certain embodiments, the system is flexible in incorporating other relevant signals besides ABP, CBFV and ICP into the database. Certain embodiments of the system allow for designing new hemodynamic feature vectors and for adopting new models for ICP estimation.

While the embodiments of the systems and methods disclosed herein relate to estimating ICP values through noninvasive procedures, these methods and systems can be used in determining other conditions, and any other random variable may be estimated using these systems and methods. For example, risks of disease or mortality, or other physiological parameters than ICP, particularly those that vary with respect to time, can be estimated through the systems and methods disclosed herein. Additionally, in the present disclosure, ABP and CBFV are used as exemplary physiological parameters from which biological signal data is obtained. However, ABP and CBFV are provided as only examples throughout this disclosure, and other physiological parameters can be measured and utilized in accordance with the systems and methods described herein.

In some embodiments, the systems and methods estimate CBFV values through noninvasive procedures. In some embodiments CBFV values are estimated from, for example, ICP and ABP values. Such a system is particularly advantageous because ICP values can be continuously recorded while CBFV assessment via transcranial Doppler may not be used continuously for an extended period of time.

Some systems for simulating ICP using various biological signal data preferably comprises a training process and a simulation process. In some embodiments, the training process first organizes biological signal data stored in a signal database into a mapping function so that the signal database is searchable. In certain embodiments, a "database" is meant to include, without limitation, a collection of information stored on an electronic device, such as a computer or computer disk.

The simulation process preferably constructs a hemodynamic feature vector from selected ABP and CBFV data and then queries the signal database by inputting the hemodynamic feature vector into the database's mapping function. The signal database may then return the an appropriate biological signal data record that may be used for building an ICP estimation model. The simulation may simulate the ICP estimation model in order to obtain unobserved ICP data.

Compared to other implementations of NICP assessment, such as MR imaging, transcranial Doppler (TCD) based approaches measuring the displacement of the skull and substituting inner ear pressure for ICP are usually the most cost effective. Furthermore, given the fact that invasive ICP is still indispensable for the purpose of treating intracranial hypertension via diverting cerebrospinal fluid, the data mining approach originated in a neurosurgical environment may advantageously build up a properly sized database to conduct a NICP assessment for other services. Data mining may thus make full use of the data collected, while other data-independent approaches cannot directly use these data sets.

As compared to the existing methods, the proposed system has the main advantage of being flexible in many aspects. Firstly, in certain embodiments, the proposed system does not attempt to build an ICP simulation model by pooling all training data. Instead, in certain embodiments, an intermediate minimum-dissimilarity driven query can be used for discovering the most appropriate entry for building ICP simulation model. Therefore, in certain embodiments, the proposed system can enjoy the flexibility of accommodating a database of diversified entries. On the other hand, pooling all training data for building an ICP simulation model may require the homogeneity of the training database. Secondly, the system is capable of responding to different requirements for noninvasively assessing various aspects of ICP by designing different dissimilarity measures and associated mapping functions. Thirdly, in certain embodiments, the system is versatile in incorporating different implementations of its various component blocks without much interference from each other. For example, the adoption of a new set of hemodynamic features does not require the change to the models chosen for ICP simulation. In this way, each block can be improved individually to enhance the overall system performance. Finally, in certain embodiments, the proposed system provides an estimate of the quality of NICP assessment—the estimated dissimilarity. Thus, a user can choose to disregard a NICP estimate if its associated dissimilarity exceeds certain limit. In certain embodiments, the system as disclosed herein may complement other existing proposals of NICP assessment.

Training Process

FIG. 1 illustrates a diagram of a training process 100 for the noninvasive intracranial pressure estimation system according to certain embodiments.

The training process moves from begin state 100 to state 101, wherein a loop begins for each entry x in a signal database. In certain embodiments, the training process 100 accesses a signal database capable of storing biological data signals. In certain embodiments, the signal database can store biological data signals such as ABP signals, CBFV signals, and invasive ICP signals. The signal database can store other relevant signals, such as $PC_{O_2}$, ECG, arterial $PO_2$, etc. A simultaneous record of signals can be stored as a single database entry, and in some embodiments, a simultaneous record of the signals can be stored as multiple database entries. In certain embodiments, the length of each entry is long enough to facilitate the extraction of low frequency information, and in some embodiments, the length of each entry is short enough to be reasonably treated as coming from a dynamic system with constant parameters.

In some embodiments, each entry in the signal database can contain two types of signals, desired signals and related signals. For example, in certain embodiments, and as illustrated in FIG. 1, invasively measured ICP can be a desired signal and other variables, including ABP and CBFV, are related signals. In certain embodiments, and as illustrated in the simulation process 500 illustrated in FIG. 5 and described further below, related signals would be made available while desired signals, such as ICP, would be estimated from the related signals.

For each entry x in the signal database, the training process in state 103 creates an ICP simulation model Mx. In certain embodiments, a simulation model is created by a simulation modeler. In certain embodiments, the simulation modeler builds a model directly from a given set of input-output data. For example, in the embodiments illustrated in FIGS. 1 and 2, the simulation modeler can build a model used for simulating ICP. In other words, the input data are biological data values such as ABP values and CBFV values, and the output is ICP. In certain embodiments, the term "values" may represent a single biological data value. In certain embodiments, the term "values" may represent more than one biological data value. In certain embodiments, the input-output data of simulation modeler and ICP simulation models are independent from certain other feature of the simulation system. Consequently, a greater flexibility has been introduced into the system by this modularity.

There are a large number of classes of dynamic models for use by the simulation modeler, including both discrete-time and continuous-time, linear and nonlinear ones, that can be used for simulating ICP given ABP and CBFV as input. In certain embodiments, a discrete linear dynamic system may be used, as further discussed herein. Specifically, as discussed herein, a stable deterministic linear dynamic model can used to represent the input/output relationship between ABP, CBFV and ICP. In certain embodiments, a nonlinear dynamic model may be used instead of a linear model. Identification of the stable deterministic linear dynamic model may be conducted using the subspace identification method. This algorithm is able to identify, given input/output data, the following state space model:

$$x_{n+1} = Ax_n + Bu_n + w_n$$

$$y_n = Cx_n + Du_n + v_n \quad (2)$$

with $$E\left[\begin{pmatrix} w_p \\ v_p \end{pmatrix} (w_k \ v_k)\right] = \begin{pmatrix} Q & S \\ S^T & R \end{pmatrix} \delta_{pk} \quad (3)$$

where A, B, C, and D are system matrices to be identified $y_n$ is the model output at time n, i.e., ICP, and $u_n$ is the model input including ABP and CBFV. $w_n$ and $v_n$ are zero-mean, stationary Gaussian white noise series, hence $\delta pk=0$ if $p \neq k$. They are termed state noise and observation noise, respectively. A key to the subspace identification algorithm is the proof that unknown state variable $x_n$ as well as its dimension can be estimated from block Hankel matrices formed from the input and output data. With estimated $x_n$ available, remaining matrices A, B, C, D, Q, S, and R, S and can be estimated using the well established linear least squares method. Therefore, two major steps of a subspace identification include: 1) estimation of model dimension and sequence of $x_n$, usually by projecting the row space of data block Hankel matrices and then applying singular value decomposition; and 2) solving a least squares problem to obtain unknown model matrices. Three major variants of subspace algorithm exist that include Multivariable Output-Error State Space (MOSEP), Canonical Variate Analysis (CVA), and Numerical algorithms for Subspace State Space System Identification (N4SID). In certain embodiments, the implementation of the subspace algorithm in the System Identification Toolbox found in Matlab 7.0 can be used. This implementation contains automatic procedures of selecting prediction horizon based on Akaike information criterion (AIC), selecting either MOSEP or CVA algorithm, and determining model dimension based on SVD. Details of this implementation can be found in the text book L. Ljung, *System identification: theory for the user*, in: Prentice Hall information and system sciences series, second ed., Prentice Hall PTR, Upper Saddle River, N.J., 1999, the entire contents of which is incorporated herein by reference.

After the simulation model is created in state 102, the training process 100 moves begins a nested loop in state 103 for each remaining entry y in the signal database. For each remaining entry y in the signal database, the process moves to state 104 wherein the ICP simulation model described earlier, Mx, is simulated against related signals for each remaining entry y in the signal database in order to obtain estimated ICP for each remaining entry y. In certain embodiments, the simulation may take place as described above, with reference to the creation of ICP simulation models. The estimated ICP output by the simulation of state 104 is then used in state 105 to calculate the dissimilarity Ey between the estimated ICP and the original ICP of each remaining entry y.

In certain embodiments, dissimilarity measures the distance between simulated and measured ICP, or other physiological variable, for a given criterion. In certain embodiments, having the mapping function output different types of dissimilarity measures makes the resultant NICP close to a particular aspect of ICP. In some embodiments, dissimilarity is used as a quality indicator of the estimated ICP even without knowing the true ICP, and thus, helps a user to decide whether to accept the estimated ICP. This flexibility is highly desirable. While the terms "measure" and "value" have their ordinary meaning, they sometimes used interchangeably herein. While this disclosure expresses the difference between estimated and observed or unobserved variables as a dissimilarity value or measure, this difference may also be expressed as a similarity value or measure, which may be, for example, the inverse or reciprocal of a dissimilarity value or measure. Thus, as used herein, the term "dissimilarity" is meant also to encompass, without limitation, the concept of "similarity."

As is well known to those of skill in the art, ICP data comprises several components, each of which may suit different clinical purposes. For example, mean ICP is still the most clinically relevant parameter that affects many clinical decisions. Pulsatile ICP has been proposed to characterize intracranial compliance. On the other hand, slow waves in ICP might provide autoregulation status of the cerebral vascular bed. The adoption of different dissimilarity measures also embodies a "divide-and-conquer" strategy in that simulating different aspects of ICP separately can result in a complete ICP assessment.

In certain embodiments, the dissimilarity measurement calculation module 130 is configured to match a simulated ICP with an unobserved ICP in a particular aspect.

In certain embodiments, dissimilarity measurement calculation module 130 uses a first metric defined as:

$$e^{(1)} = \frac{1}{N} \frac{\sum_{i=1}^{N} |y_i - \hat{y}_i|}{|\bar{y}|}. \quad (4)$$

where N is number of samples $y_i$ is the $i^{th}$ sample of unobserved ICP waveform and $\hat{y}_i$ its corresponding estimate. $e^{(1)}$ calculates the mean absolute error between a signal y and its estimate $\hat{y}$ normalized by the mean of signal $\bar{y}$. This is a comprehensive metric in the sense that both the mean value and waveform shape of $\hat{y}$ have to be close to those of y in order to achieve a small $e^{(1)}$.

In certain embodiments, dissimilarity measurement calculation module 130 uses a second metric defined as:

$$e^{(2)} = \frac{|\bar{\hat{y}} - \bar{y}|}{|\bar{y}|} \quad (5)$$

This metric calculates the normalized absolute error between the mean estimated ICP and the mean original ICP. This is motivated because the mean is still the most used information for clinicians in which case the shape of the waveform might not be a concern.

In certain embodiments, dissimilarity measurement calculation module 130 uses a third metric defined as:

$$e^{(3)} = 1 - \text{corr}(y^N, \hat{y}^N), \quad (6)$$

which lies in the range [0, 2]. corr(x, y) is the operator for calculating the zero-lag cross correlation coefficient between x and y. This metric excludes the effect of mean signal level and puts more emphasis on the matching of the two signals in their general trend. To calculate $e^{(3)}$, it was found advantageous to derive $\hat{ICP}$ using normalized ABP and CBFV in both model identification and simulation phase. Thus $y^N$ stands for the normalized ICP and $\hat{y}^N$ its estimate. The normalization of a signal x was carried out as $$x^N = \frac{x - \bar{x}}{\bar{x}} \quad (7)$$

In certain embodiments, dissimilarity measurement calculation module 130 uses a fourth metric defined as:

$$e^{(4)} = \frac{\sum_{i=1}^{N} |y_i^P - \hat{y}_i^P|}{N|y^P|}. \quad (8)$$

where $y^P$ represents the pulsatile component of signal y and denotes $|y^P|$ denotes the average amplitude of the pulse. Hence, this measure emphases matching the pulsatile component. As for deriving $e^{(3)}$, $ICP^P$'s estimate was derived by using corresponding pulsatile components of ABP and CBFV for model identification and simulation. Understandably, such models were different from those used in calculating $e^{(3)}$, which were built using normalized signals.

In certain embodiments, in order to match slow wave components, the dissimilarity measurement calculation module 130 can use a fifth metric defined as:

$$e^{(5)} = \frac{\sum_{i=1}^{N} |y_i^S - \hat{y}_i^S|}{N|y^S|} \quad (9)$$

where $y^S$ represents the slow-wave component of signal y and denotes $|y^S|$ denotes the mean of $y^S$. Similarly, $\hat{ICP}^S$ was derived by building and simulating the linear dynamic model using slow wave components of ABP and CBFV.

Upon calculating dissimilarity Ey in state 105, the process moves to state 106, wherein Ey is accumulated into an one-dimensional array E. Thus, after the nested loop has completed running through each remaining entry y in the signal database, the one-dimensional array E will store a dissimilarity value Ey calculated using entry x and each remaining entry y in the database, according to the process being discussed. In certain embodiments, any appropriate data structure may be used to store array E, including, but not limited to, an array, vector, list, and/or matrix.

The process 100 then moves to state 107 where through signal analysis a hemodynamic feature vector Fy is extracted from related signals stored for each remaining entry y in the signal database.

In certain embodiments, signal analysis describes a procedure or process for extracting a hemodynamic feature from biological signals. In certain embodiments, signal analysis is not applicable to ICP signals. In certain embodiments, signal analysis can extract hemodynamic features from biological data signals because cerebral hemodynamics are under the influence of cerebrospinal fluid (CSF) dynamics, and thus a suitable hemodynamic feature might carry information that could be used as a probe to CSF dynamics. Consequently, the designed hemodynamic features should be able to characterize the unique aspect of hemodynamic state that can be attributed to the effect of CSF dynamics.

In certain embodiments, several ways of constructing hemodynamic features from measurements of ABP values and CBFV can be used, including, but not limited to, Slow Wave Dynamics, Waveform Analysis, and Full Dynamics.

For slow wave dynamics, slow wave components having a frequency below heart rate have been identified in ABP, CBFV, and ICP in previous studies. They may have different physiological origins and interact with each other in a non-trivial fashion. Of interest here is that slow waves in CBFV carry information regarding how the cerebral vascular bed responses to the slow waves present in ABP and ICP.

To extract the slow wave component, a beat-to-beat average of corresponding signal was first extracted and resampled, using a cubic spline, at 2 Hz. Each beat was delineated using ABP waveform and the results were visually checked. To extract a hemodynamic feature vector from these signals, a linear autoregressive model with exogenous input (ARX) can be fitted to the output/input pair of CBFV/ABP and the resultant model coefficients can be used as hemodynamic feature vectors. In certain embodiments, a linear dynamic system is adequate for modeling the input/output relationship between slow waves of ABP and CBFV that were extracted in a similar way. Model orders can be determined as the median of optimal model orders found for all signal entries. Minimum description length (MDL) criterion was adopted for determining optimal order for each entry. For an easy reference, the hemodynamic feature thus created is denoted as $F_{slow}$.

By resorting to waveform analysis, the following measures can be extracted in a beat-to-beat fashion: Trans Systolic Time (TST), Resistance Area Product (RAP), Critical Closing Pressure (CCP), CBFV Pulsatility index (PI), Resistance Index (RI), mean FV (mFV), amplitude of the FV (pFV), systolic FV (sFV) and diastolic FV (dFV).

The extraction procedure can result in a beat-to-beat time series for each measure. Two types of hemodynamic features can be derived from these time series. The first type is static in the sense that mean and the standard deviation of the each time series is cascaded into a hemodynamic feature denoted as ($F_{sta}$). On the other hand, to derive the second type of hemodynamic feature, an autoregressive model (AR) is fitted to each secondary time series and the model coefficients are cascaded into a hemodynamic feature designated as ($F_{dyn}$). The AR model order can be determined using the same procedure.

In contrast to the procedures mentioned above where slow wave components extracted from original signals were used for feature extraction, a full dynamic feature can be constructed based on the raw waveforms. Specifically, an ARX model can be adopted with a higher model order to fit each CBFV and ABP pair. Two kinds of feature vectors can then derived from the model coefficients. As known from system theory, two transfer functions for two outputs of a linear dynamic system with the same input should share a common denominator, which determines the inherent system properties such as resonant frequencies. In the present context, the coupled cerebral hemodynamic and intracranial hydraulic systems can be treated as one system with ABP as its input and CBFV and ICP as its output. Thus, in certain embodiments, the feature vector composed solely of the ARX denominator coefficients can be a better characterization of the properties of the combined system by excluding what is specific to the ABP→CBFV transfer function. This feature vector was denoted as $F_{den}$. In certain embodiments, a second feature denoted as $F_{full}$ composed of all the model coefficients can also be also included.

In certain embodiments, hemodynamic features with less inter-patient separability are more appropriate for being used as hemodynamic features. Since LDA projection can be used to remove patient-specific discriminant feature directions, in certain embodiments, pre-processing of feature vectors may improve NICP assessment.

In certain embodiments, one important property of various feature vectors is their separability in the feature space. For pattern classification purposes, in certain embodiments, a feature set with good separability is desirable. In certain embodiments, separability might have to be treated differently because the hemodynamic features extracted can be used as the input to a continuous mapping function, as illustrated. Due to this requirement of continuity, it is more difficult to obtain a continuous mapping function from such a disjoined data set for well separated feature vectors.

To further elaborate, say, for example, each patient may become a class. A class-independent linear discriminate analysis (LDA) can be performed to reduce the dimension of the original feature vector for the purpose of visualization as well as to quantify its inter-patient separability. This can be achieved by solving the following generalized eigenvalue decomposition.

$$S_b a_i = \lambda_i S_w a_i, \lambda_1 \geq \lambda_2 \geq \ldots \geq \lambda_m \quad (1)$$

where $S_b$ is the between-class covariance matrix of the hemodynamic features, $S_w$ the within-class covariance matrix, and $\lambda_i$ is the ith eigenvector. m is the dimension of the original feature space. $a_i$s are the generalized eigenvectors. In certain embodiments, the leading three of these values can give the directions of the subspace where the original feature will be projected onto for visualization. $\lambda_i$ is positively proportional to the degree of separability of the features along $a_i$, thus different feature sets' separability can be compared based on $\lambda_i$s. $S_b$ and $S_w$ can be obtained in the usual way, as found in X. Hu, V. Nenov, *Multivariate ar modeling of electromyography for the classification of upper arm movements*, Clin. Neurophysiol. 115 (6) (2004) 1276-1287, which is hereby incorporated in by reference in its entirety.

Hemodynamic feature $F_{slow}$ can be extracted from ARX model coefficients, as discussed above. In certain embodiments, the order is (6, 2) for the denominator and the numerator polynomials of the transfer function, respectively. $F_{dyn}$ can be extracted from nine AR models. The order of each model was determined as 4. $F_{full}$ and $F_{den}$ can be extracted from an ARX model with orders (8, 24).

Figure 2:
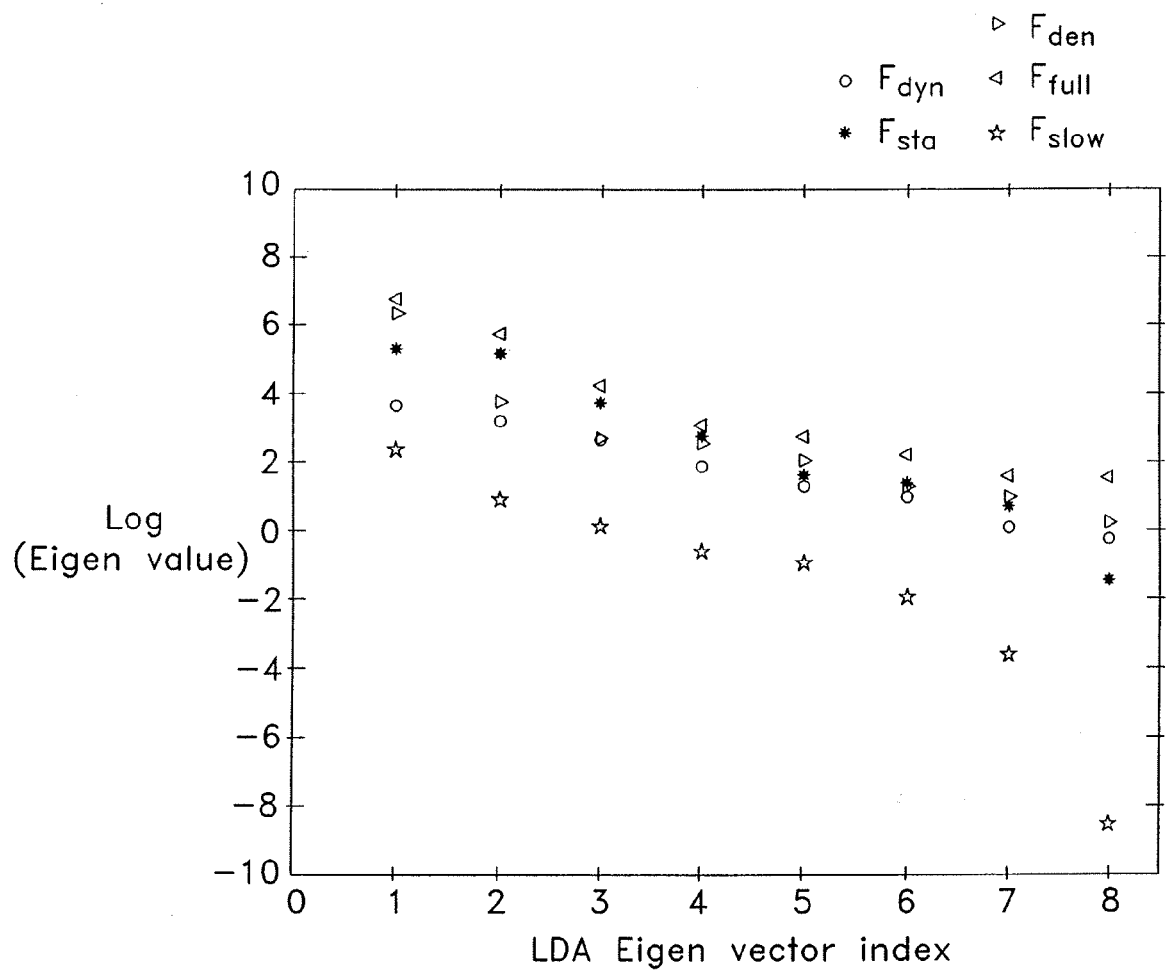
FIG. 2 illustrates a logarithm of the linear discriminant analysis eigenvalues of the five types of hemodynamic features investigated in the paper.
Figure 3:
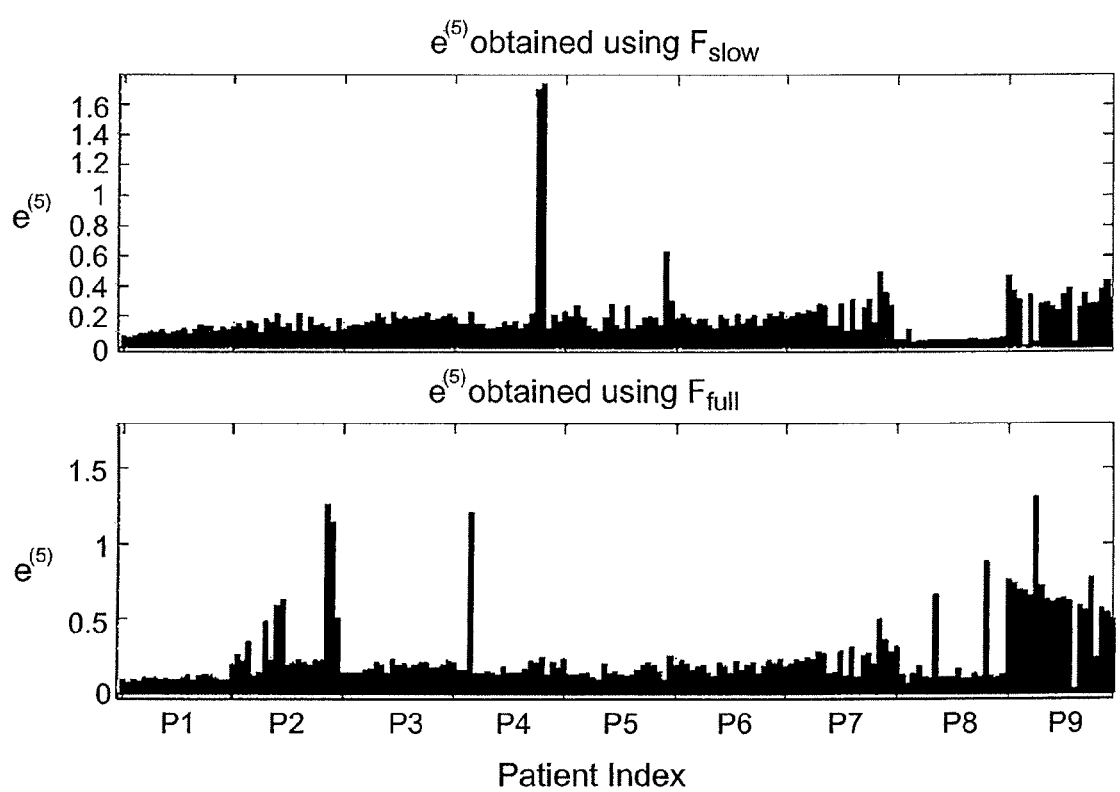
FIG. 3 illustrates a comparison of the $F_{slow}$ and $F_{full}$'s performance of NICP assessment based on dissimilarity measure $e^{(5)}$, which was obtained in a leave-one-patient-out fashion using the robust query method.

LDA eigenvalues of five types of hemodynamic features are presented in FIG. 2. As illustrated, the eigenvalues of each feature type are positively proportional to the separability of the feature along the corresponding eigenvectors' directions. $F_{slow}$ has the lowest patient separability while $F_{full}$ is the most discriminant one. $F_{den}$ is less discriminant than $F_{full}$ since the later contains the former. To test which type of feature will be more appropriate for being used as input to mapping functions, a leave-one-patient-out validation was conducted based on $e^{(5)}$ using $F_{full}$ and $F_{slow}$ as input to the mapping function, respectively. The final $e^{(5)}$ achieved for both of them is presented in FIG. 3, which is a comparison of $F_{slow}$ and $F_{full}$'s performance of NICP assessment based on dissimilarity measure $e$ð 5Þ . Overall $F_{slow}$ achieved smaller $e^{(5)}$ except for two data entries from patient No. 4. This analysis indicates that hemodynamic features with less inter-patient discriminant ability can be used as the input to the mapping function. In certain embodiments, according this result, the rest of the computations will be based on $F_{slow}$. In certain embodiments, computations may be based on other feature types.

In certain embodiments, there are four different ICP simulation models that can be identified using the system identification method described above. To calculate $e^{(1)}$ and $e^{(2)}$ the model can be built using unfiltered ABP, CBFV and ICP; normalized signals will be used to calculate $e^{(3)}$; pulsatile components of signals will be used to calculate $e^{(4)}$; slow-wave components will be used for $e^{(5)}$. This design of various dissimilarity measures reflects possible requirements that a NICP assessment method might have to satisfy. The correlation among those measures are very low by design, hence, in certain embodiments, different ICP simulation models and different mapping functions can be built for them.

After extracting the hemodynamic feature vector Fy in state 107, the training process moves to state 108 where the hemodynamic feature vector is accumulated into a two-dimensional array F, the ith row of which (array Fy) is dissimilarities between the ith model simulated ICP and the measured ICP of all the data entries in the signal database. This row vector, Fy, thus serves as the output of the training data set to learn the mapping function for the ith data entry.

The training process then moves to state 109 wherein the nested loop continues to run for each remaining entry y as compared to entry x in the signal database.

After the nested loop defined between states 103 and 109 completes for entry x, the process moves to state 110 wherein a mapping function MFx is trained by using a training algorithm, where the two dimensional array F is input, and the one-dimensional array E is output.

In certain embodiments of the training process 100, a mapping function associates each entry in the signal database with a mapping function. In certain embodiments, the mapping function associated with an entry can take a hemodynamic feature vector, such as Fy, as input and output a dissimilarity measure, such as Ey. In certain embodiments, a dissimilarity measure represents the distance between the simulated and the measured ICP for a given criterion, as discussed above. Consequently, a mapping function can predict how well a simulation model built from a database entry will perform in simulating ICP for signals whose hemodynamic feature vectors are input to the mapping function.

In the embodiment illustrated, the input to the mapping function comprises an array of hemodynamic features. The predicted dissimilarity serves two purposes: (1) guide the database query, i.e., queries which appear to achieve less simulation error will be returned upon query; and (2) provide an estimate of the final quality of the NICP simulation.

In certain embodiments, the first step to obtain mapping function MFx is to perform a complete cross-validation of the database entries. In certain embodiments, validation can be carried out using a leave-one-patient-out schema. Accordingly, to proceed with the leave-one-patient-out schema, certain illustrated examples herein use certain embodiments of implementing mapping function MFx trained using the data from eight patients and tested on the remaining one.

Specifically, one embodiment of the proposed system was implemented using a database of nine traumatic brain injury patients. Each patient had a thirty-minute long passive recording of ABP values, ICP values, and CBFV values. CBFV values were obtained at the right middle cerebral artery, ipsilateral to the ICP measurement location, with ultrasonography transducers fixed to a headband to prevent motion artifacts. ABP values were measured through radial A-lines while ICP values were measured using a ventricular catheter connected to an external strain gauge. All three signals were fed into bedside multi-modality monitors, which were then simultaneously sampled at 75 Hz using a data acquisition system equipped with proper interfaces to the bedside patient monitors. The criterion for selecting the nine patients was that their archived data included continuous measurements of ABP values, ICP values, and CBFV values. Key characteristics of the patients used in the sample implementation are listed in FIG. 4.

Each 30-minute long data segment was decomposed into 20 consecutive short segments, each of which contains about 100 heart beats of data. This segment length was chosen as a compromise between the requirements of capturing long-term changes in signals and being able to treat such a segment as from a constant-parameter dynamic system.

The results obtained indicate that hemodynamic features that do not emphasize characteristics of each individual subject and the statistic query method that considers the imperfectness of the mapping function performed better for NICP simulation. The performance of the data ruining method was shown in certain embodiments to be superior to existing methods that use the same material for simulating ICP. However, considering that the signal database consisted of only nine patients' data, this result should be treated cautiously as a positive sign that motivates further evaluations with more clinical materials.

In certain embodiments, to provide comparisons to the proposed method described above, the following mapping functions were implemented according to the following published NICP methods for assessing mean ICP:

Aaslid's original proposal:

$$I\hat{C}P_m = ABP_m - \frac{CBFV_m|ABP_1|}{|CBFV_1|};\quad(14)$$

Czosnyka method:

$$I\hat{C}P_m = ABP_m - \frac{ABP_m \times CBPV_{dias}}{CBFV_m} - 14;\text{ and}\quad(15)$$

Belfort method:

$$I\hat{C}P_m = ABP_m - \frac{CBFV_m \times (ABP_m - ABP_{dias})}{CBFV_m - CBFV_{dias}};\quad(16)$$

where $|ABP_1|$ and $|CBFV_1|$ represent the amplitudes of the harmonic of ABP and CBFV corresponding to heart rate respectively. $ABP_m$ stands for the mean ABP and $ABP_{dias}$ for the diastolic ABP. The same notation applies to CBFV as well.

In addition, the method due to Schmidt and Czosnyka et al. (in B. Schmidt, J. Klingelhofer, J. J. Schwarze, D. Sander, I. Wittich, *Noninvasive prediction of intracranial pressure curves using transcranial doppler ultrasonography and blood pressure curves*, Stroke 28 (12) (1997) 2465-2472), the entirety of which is hereby incorporated by reference, capable of assessing ICP waveform can also be implemented and compared to the proposed data mining approach. In certain embodiments, modified versions of the above methods may be used.

In certain embodiments, the mapping function MFx can depend on different hemodynamic features. In certain embodiments, a flexible function approximator like a multi-layer feed forward neural network can be used. In certain embodiments, the amount of available training data should substantially match with the number of unknown parameters in the neural network.

In the implementation including nine patients described above, to train a mapping function, the number of training input-output pairs was 160 because the 20 data entries associated with the corresponding patient whose associated mapping functions are being trained were excluded for a realistic testing of the performance of the method. The smallest hemodynamic feature $F_{slow}$ had a dimension of 4. Following a typical recommendation of a two layer network configuration (as described in M. T. Hagan, H. B. Demuth, M. H. Beale, *Neural Network Design*, first ed., PWS Pub, Boston, 1996.), the entirety of which is hereby incorporated by reference, the number of hidden units at each hidden layer would be 8 and 4. This choice will result in 80 unknown network weights and biases. There will be a great probability of overfitting the network to learn these 80 unknown with 160 input-output pairs. Taking this into consideration, a linear function was selected to predict dissimilarity e given hemodynamic feature vectors F such that $$e = F^T b \quad(10)$$

where e is a scalar representing the dissimilarity output, F is a column hemodynamic vector, and b is a column coefficients vector having the same dimension as F. Given the training data set, which contains $e_i$ and $F_i$ with $i=1, \ldots, N_k$, application of a linear least squares estimation results in an estimate of b as $$\hat{b} = (F^T F)^{-1} F^T e \quad(11)$$

where $N_k$ is the total number of database entries minus the number of excluded ones and F is a $N_k \times d$ data matrix, ith row of which is $F_i^T$. e is a column vector comprised of $e_i$. Standard linear regression theory states the covariance of b as $$V_b = (F^T F)^{-1} \sigma^2 \quad(12)$$

where $\sigma^2$ is the variance of the observational noise present in e, which is usually assumed to be white Gaussian noise. This assumption leads to the result that $\hat{b}$ is normally distributed, with its mean being the unknown b and its covariance matrix being $V_b$. In certain embodiments, a statistical query can be designed based this result.

In certain embodiments, a more versatile functional form may be used to model the mapping function. Such choices may include variants of multiple-layer feedforward neural networks, radial basis networks and local linear fuzzy models. In certain embodiments, the system may use a recursive identification of dynamics through a multiple model schema, as discussed in P. Andersson, *Adaptive forgetting in recursive-identification through multiple models*, Int. J. Control 42 (5) (1985) 1175-1193, the entirety of which is hereby incorporated by reference.

In certain embodiments, TCD equipment may be configured to incorporate the database and its related algorithms. In certain embodiments, the training process can involve a significant amount of computational cost that can be shared among several computing devices, such as computing servers. In certain embodiments, computational load sharing is facilitated through the independence of the training process for individual database entries. As a result of the training process, each database entry may be associated with a mapping function that can be coded into a stand-alone library to be distributed to each client machine together with the database.

Simulation Process

Figure 5:
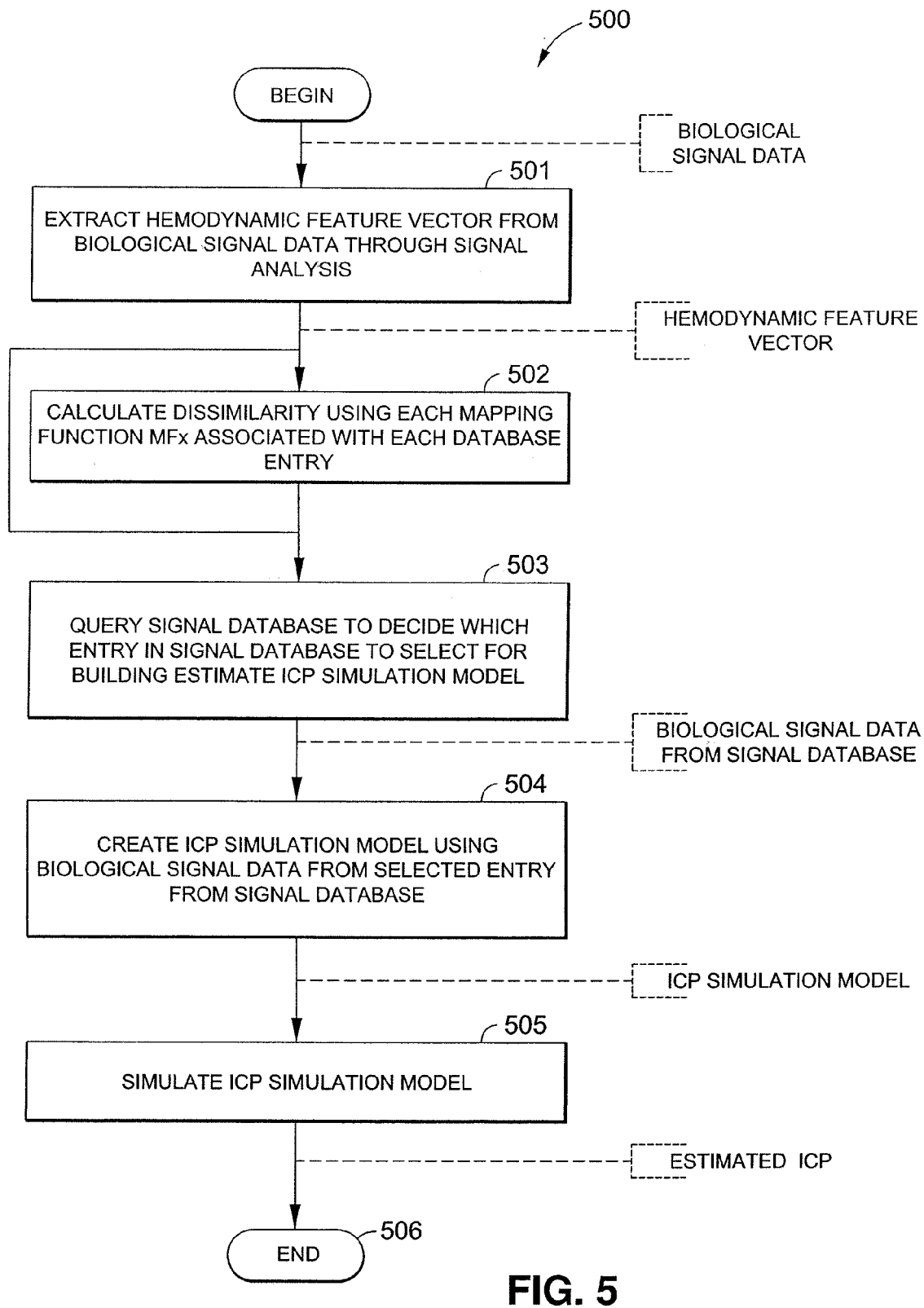
FIG. 5 illustrates a block diagram of one embodiment of the simulation process of the proposed noninvasive intracranial pressure estimation system.

FIG. 5 illustrates one embodiment of a simulation process 500 of the proposed noninvasive intracranial pressure estimation system. In certain embodiments, and as illustrated in FIG. 5, the simulation process 500 first moves from a begin state to a first state 501 wherein hemodynamic features are extracted from biological data signals, using a similar process to those discussed above with reference to state 107 of FIG. 1, thereby creating a hemodynamic feature vector. Next, the process moves to state 502 wherein the hemodynamic feature vector is input into each mapping function MFx associated with each signal database entry in order to calculate a dissimilarity measurement. In certain embodiments, the mapping function trained in the process 100 of FIG. 1, and as described above, can be used.

The process then moves from state 502 to state 503 wherein a decision is made regarding which entry in the signal database to select for building an ICP simulation model by querying the database. The hemodynamic feature vector from state 501 can also be used to query the signal database with additional dissimilarity measurement data.

In certain embodiments, based on the output of the mapping function of state 502, a decision is made as to which database entry should be selected for building an ICP simulation model. In certain embodiments, the database query returns only one database entry. In certain embodiments, the database may return a set of candidate entries and then fuses the estimated ICP from each of the models identified from the set. In certain embodiments, the decision of state 503 can accommodate multiple implementations. For example, in certain embodiments, the hemodynamic feature vector and dissimilarity measurement data can be fed into the mapping function associated with each signal database entry, and, based on each of the mapping functions' output, a decision can to be made with regard to which entry is to be returned in response to the query. In certain embodiments, the decision process can select the database entry with the smallest predicted dissimilarity for building the simulation model. In certain embodiments, the decision process can incorporate high-level information regarding the database entries. Such high-level information can include, for example, clinical symptoms and observations of the patients, and the temporal closeness of two database entries. In certain embodiments, further statistical information of the mapping function output, such as its variance, can also be incorporated by the decision process of state 503 when making a decision.

In certain embodiments, other approaches may be used in order to decide which signal database entry to select for building the ICP simulation model, such as a statistical decision maker. Let $\hat{b}$ be a random variable and normally distributed with the true b being its expectation and $V_b$ its covariance matrix. The output of a mapping function $e_i = F_i^T \hat{b}$ would thus be a normal random variable with its mean being the true mapping function output $F_i^T b$ and its variance being $F_i^T V_b F_i$. Furthermore, assume that outputs from different mapping functions are independent. This leads to the conclusion that the variable $e_i - e_j$, $i \neq j$ is also normally distributed with $F_i^T b - F_j^T b$ being its mean and $F_i^T V_b F_i + F_j^T V_b F_j$ being its variance. With this result, the standard z value for testing the difference between $e_i$ and $e_j$ can be computed as $$z_{i,j} = \frac{e_i - e_j}{\sqrt{F_i^T V_b F_i + F_j^T V_b F_j}}. \tag{13}$$

A score can be assigned to $e_i$ as the number of positive hypothesis test that $e_i$ is smaller than $e_j$, $j=1,\ldots,n$ using $z_{i,j}$. In certain embodiments, the entry that achieves the maximal score will be selected.

Figure 6A:
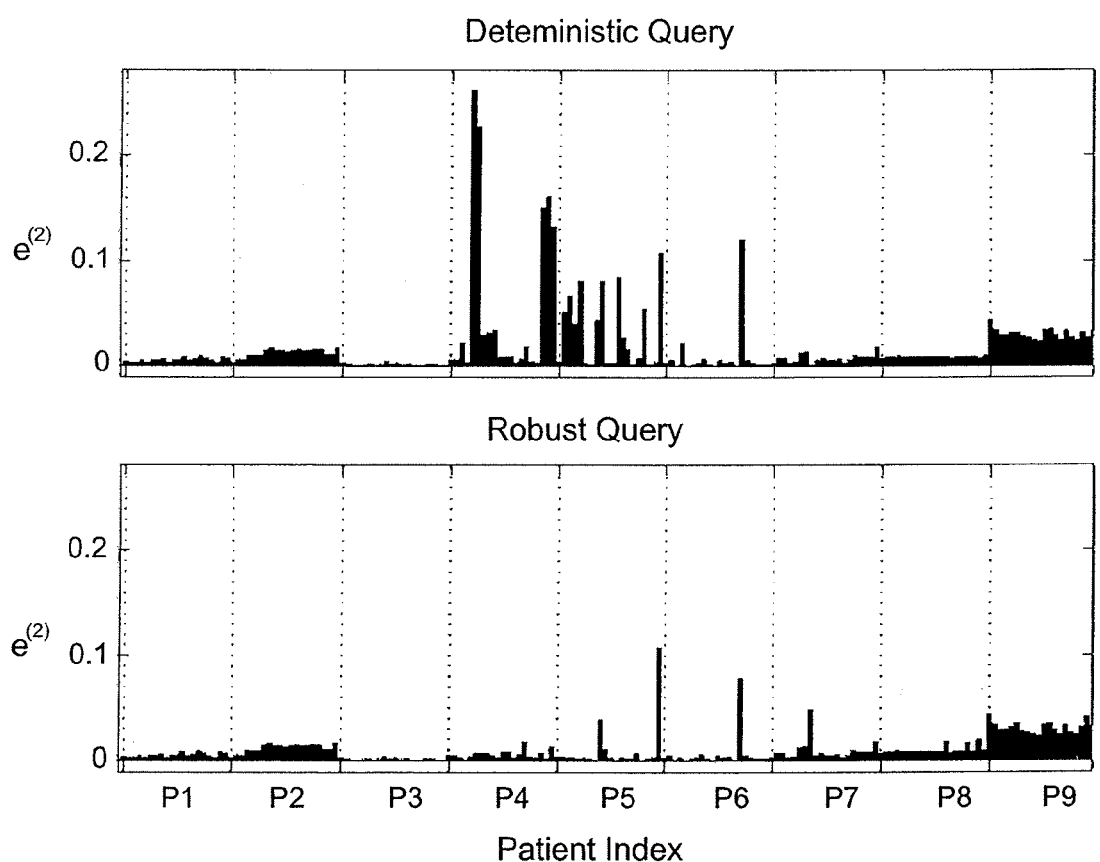
FIG. 6A illustrates a comparison of the deterministic and the statistical query methods based on $e^{(2)}$, which was obtained using CBFV as model input.
Figure 6B:
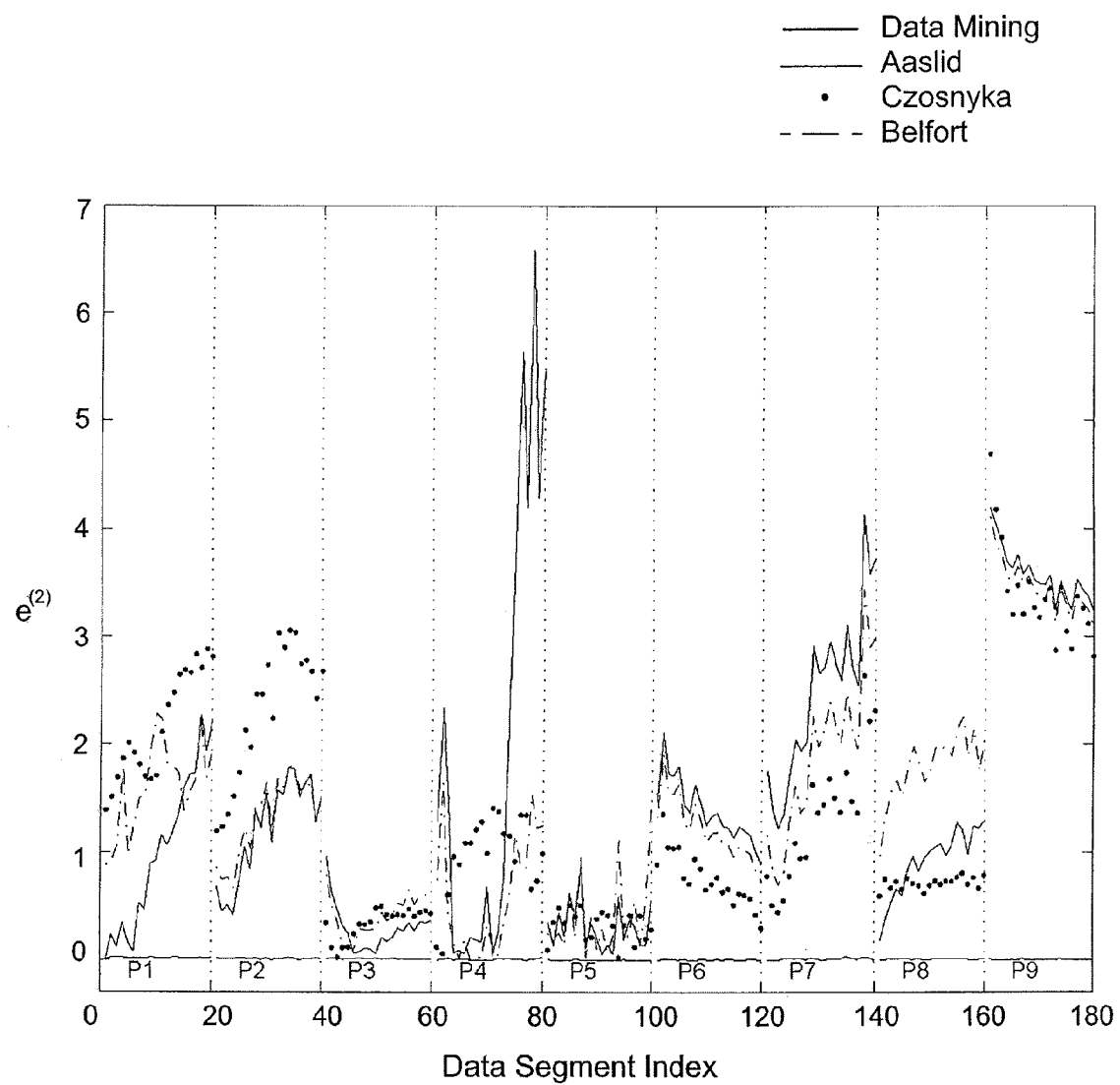
FIG. 6B illustrates another comparison of the relative error in assessing the mean ICP obtained using the proposed data mining approach to those obtained using three published NICP assessment methods according to certain embodiments.

In certain embodiments, the signal database is queried in state 503 in order to make a decision regarding which entry to select for estimated ICP model simulation in state 504, which is then simulated in state 505. In certain embodiments, in state 504, the model simulation is provided with biological data values from the entry. In certain embodiments, the means for providing the simulation model with the biological data values is through a function or procedure call including data associated with the biological data values. In certain embodiments, The performance of the deterministic and the statistical query methods is compared in FIG. 6A based on $e^{(2)}$. FIG. 6B illustrates another comparison of the relative error in assessing the mean ICP obtained using the proposed data mining approach to those obtained using three published NICP assessment methods according to certain embodiments. As illustrated, the statistical query method did improve the robustness of results by suppressing those erroneous results present for some data segments from patients 4 and 5. This observation was also true for other dissimilarity measures. For this reason, in certain embodiments, the statistical query method is used. In certain embodiments, the deterministic method can be used. In certain embodiments, other methods may be used.

Figure 7A:
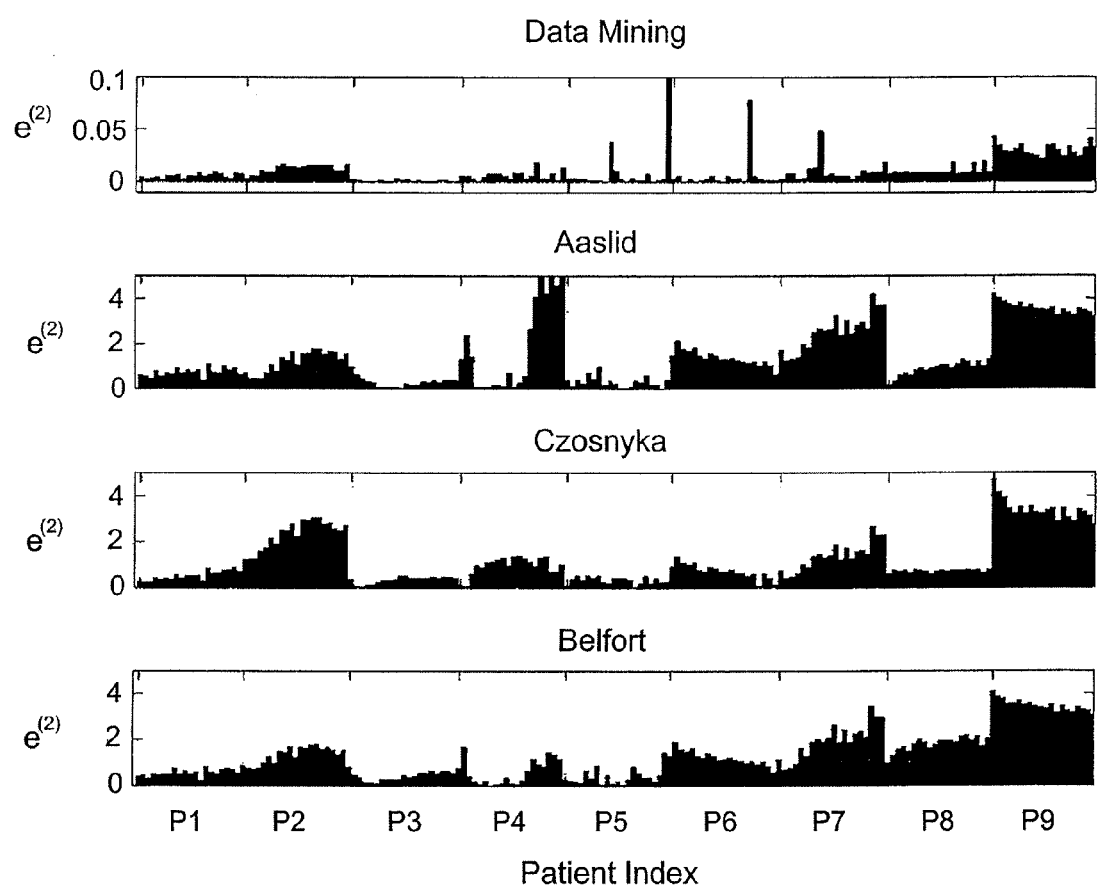
FIG. 7A illustrates a comparison of $e^{(2)}$ obtained using the proposed data mining approach to those obtained using three published NICP assessment methods.
Figure 7B:
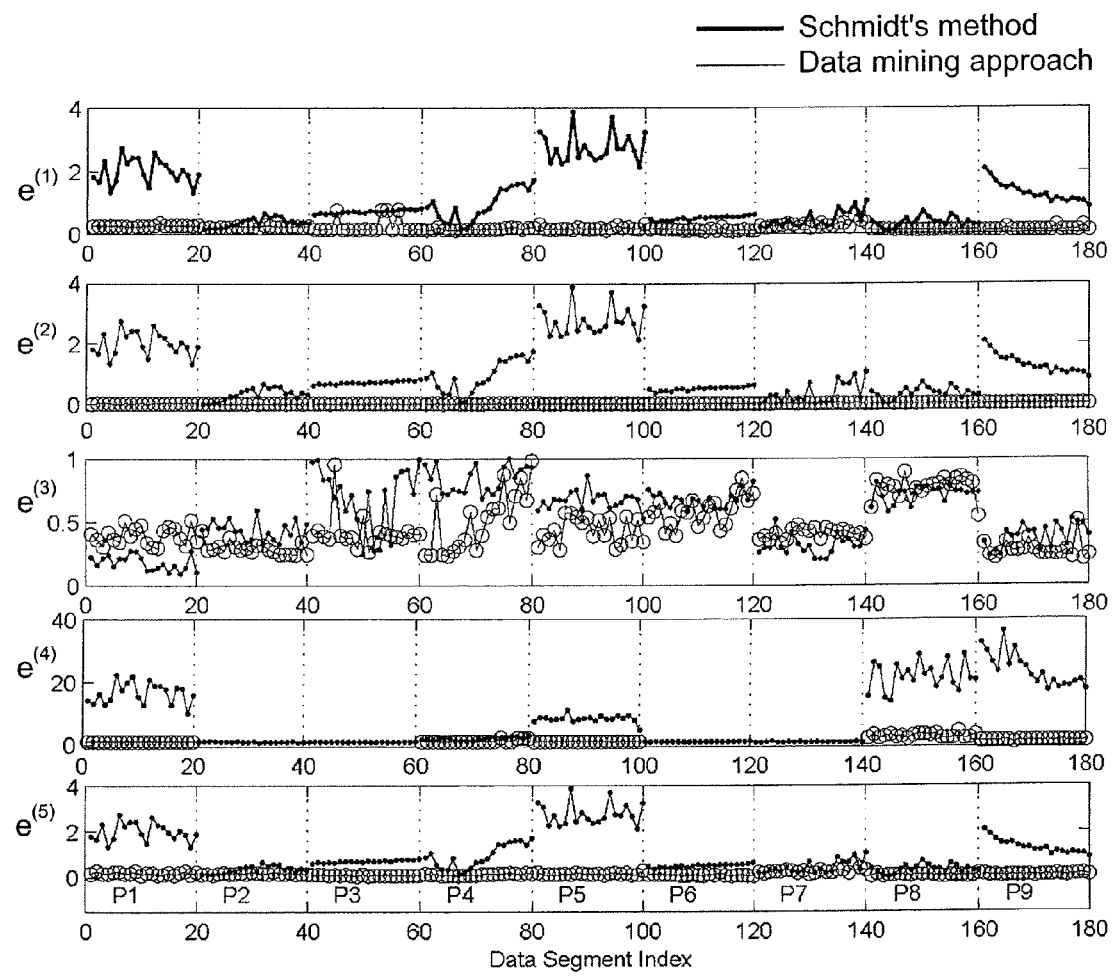
FIG. 7B illustrates another comparison of the proposed data mining approach to the published Schmidt method that can simulate ICP waveform. The comparison is based all the five defined dissimilarity measures.

In certain embodiments, and based on previous results, the proposed system uses $F_{slow}$ as the hemodynamic feature vector and the statistical query method for retrieving the appropriate data entry. Sample results from this combination are compared to the three published formulas for estimating mean ICP as shown in FIG. 7A, in terms of $e^{(2)}$. FIG. 7B illustrates another comparison of the proposed data mining approach to the published Schmidt method that can simulate ICP waveform. The comparison is based all the five defined dissimilarity measures. The results from certain embodiments of the proposed system using $F_{slow}$ as the hemodynamic feature vector and the statistical query method for retrieving the appropriate data entry as compared to Schmidt's method are illustrated in FIG. 8 based on $e^{(1)}$, $e^{(3)}$ and $e^{(5)}$.

Figure 8:
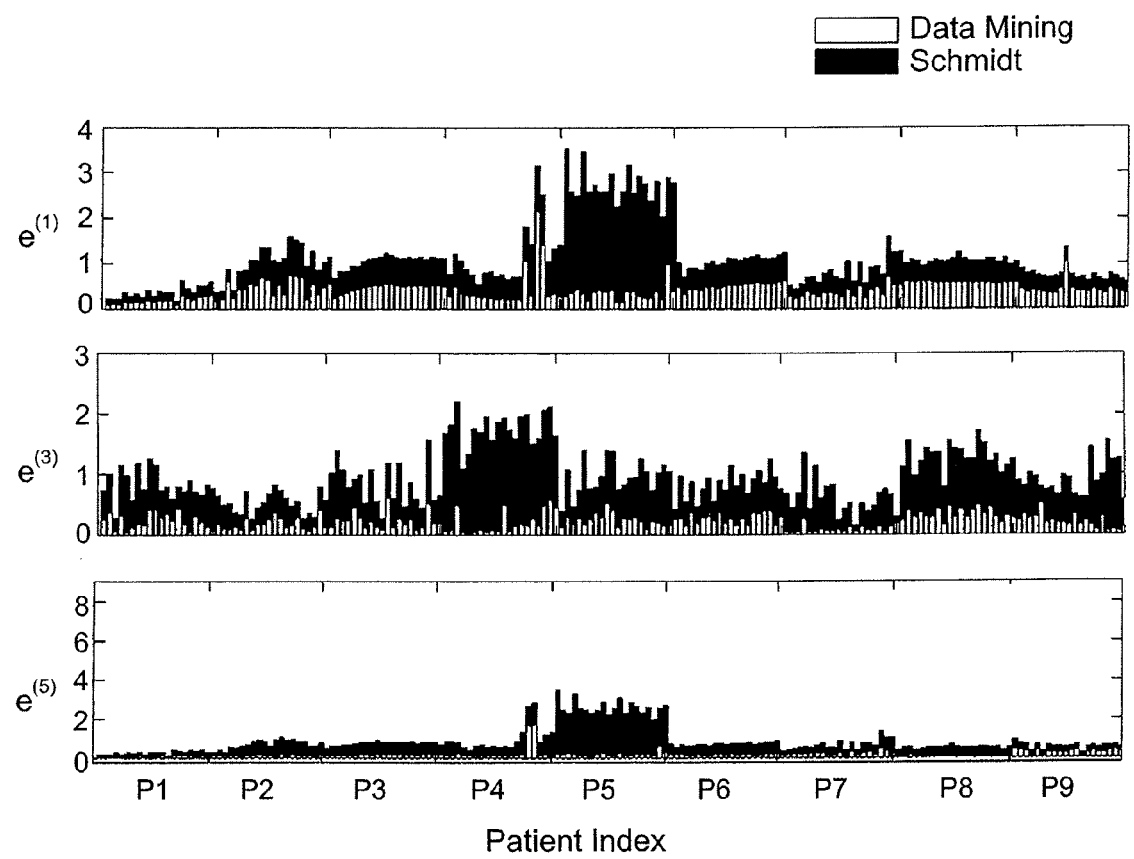
FIG. 8 illustrates a comparison of certain embodiments of the proposed data mining approach, based on $e^{(1)}$, $e^{(3)}$ and $e^{(5)}$, with the published Schmidt method that can simulate ICP waveform. $F_{slow}$ and robust query were used in the data mining approach.

As illustrated in FIG. 8, although Schmidt's method may be capable of simulating ICP waveform, the illustrated results shown here demonstrate that the proposed method outperforms Schmidt's method significantly.

Figure 9:
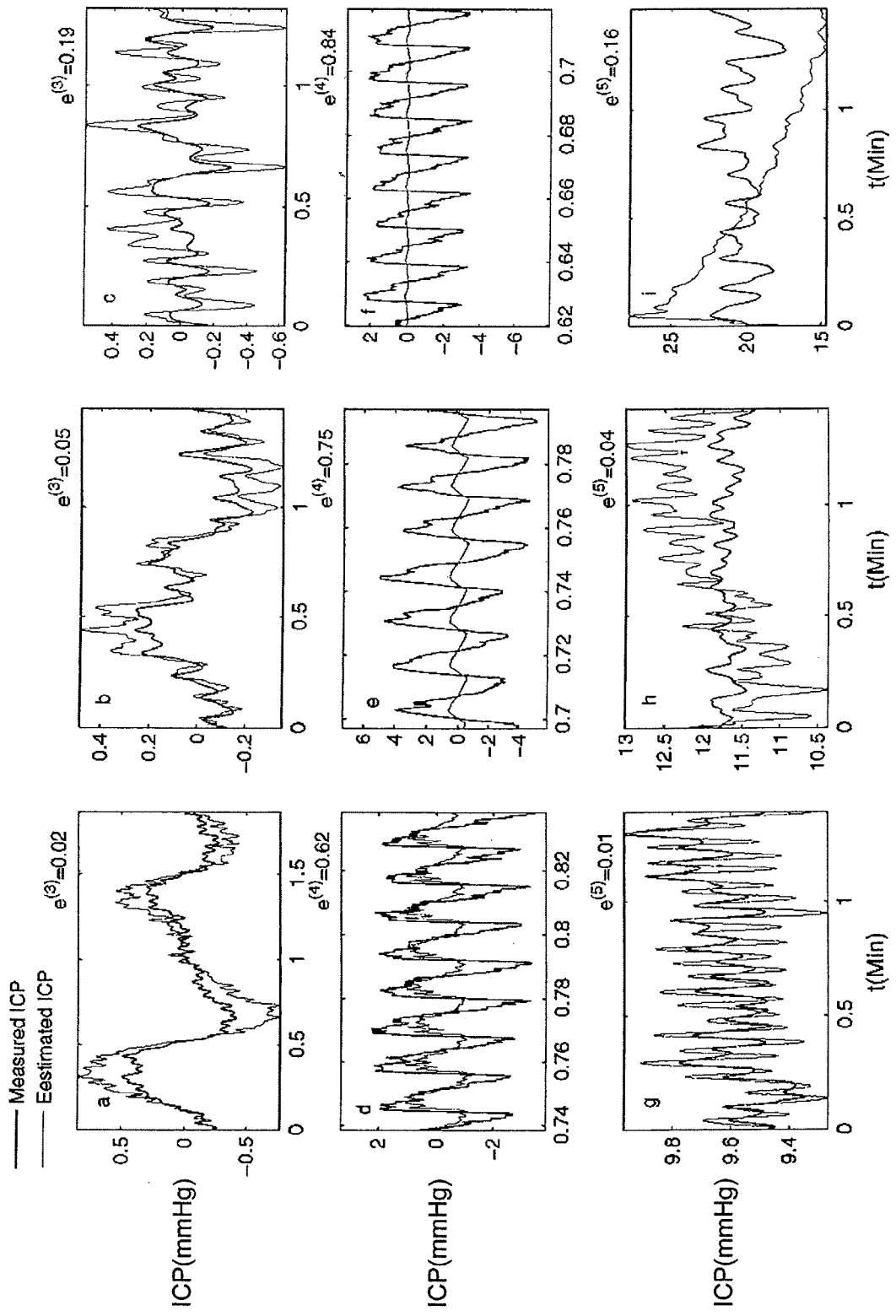
FIG. 9 illustrates a summary presentation of estimated ICP waveform based on different dissimilarity measures.

After the simulation in state 505 is complete, the simulation process 500 for estimating ICP ends at state 506. FIG. 9 gives summary plots of several comparisons between estimated ICP and measured ICP. The estimated ICP illustrated is based on different dissimilarity measure.

Panels a, b, and c display the estimated ICP and measured normalized ICP. Panels d, e, and f compare pulsatile ICP. Panels g through i illustrate the slow-wave component of ICP. Panels in the left most column, panels a, d, and g, illustrate database entries that achieved the smallest dissimilarity measure. Panels in the middle column, panels b, e, and h, illustrate panel entries that achieved a dissimilarity measure close to the 50 percentile.

Three representative database entries for each of $e^{(3)}$, $e^{(4)}$ and $e^{(5)}$ are illustrated in FIG. 9. The three representative database entries for each of $e^{(3)}$, $e^{(4)}$ and $e^{(5)}$ correspond to those entries whose dissimilarity measures are the smallest, closest to the 10 percentile, and closest to the 50 percentile, respectively. It can be seen from FIG. 9 that in certain embodiments waveforms of estimated and measured normalized ICP are close to each other, while the matching of waveforms based on pulsatile ICP components is poor, even for entries with smallest dissimilarity.

Figure 10:
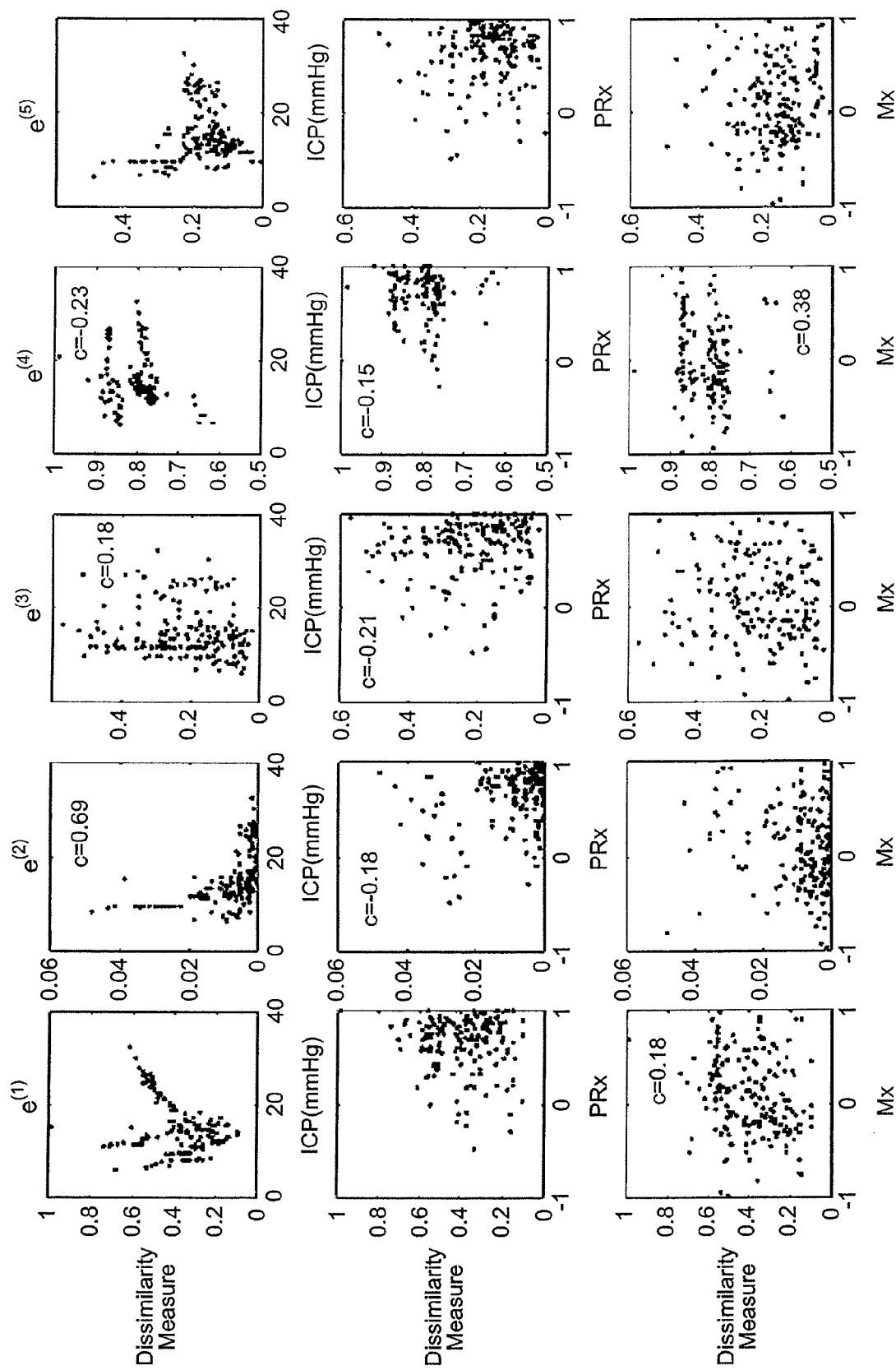
FIG. 10 illustrates scatter plots of dissimilarity measures as a function of mean ICP (the first row), PRx (the second row) and Mx (the third row), respectively.

The influence of mean ICP and pressure autoregulation status on the performance of ICP estimation was investigated in the embodiment of the system implemented using nine patients, as described above. To characterize pressure autoregulation status, two existing measures including PRx and Mx were calculated. Average ABP, CBFV, ICP and CPP (as described in M. Czosnyka, P. Smielewski, P. Kirkpatrick, D. K. Menon, J. D. Pickard, *Monitoring of cerebral autoregulation in head-injured patients*, Stroke 27 (10) (1996) 1829-1834; and M. Czosnyka, P. Smielewski, P. Kirkpatrick, R. J. Laing, D. Menon, J. D. Pickard, *Continuous assessment of the cerebral vasomotor reactivity in head injury*, Neurosurgery 41 (1) (1997) 11-17 (discussion 17-9)) were first computed using a running 10-second window. Then PRx and Mx were calculated as the cross-correlation coefficient between consecutive averaged values of ABP and ICP, and CPP and CBFV, respectively. Thus each database entry is associated with a PRx and a Mx measured indicating their pressure autoregulation status. In addition, mean ICP of each database entry was also calculated. Results are presented in FIG. 10 as scatter plots where mean ICP, PRx and Mx were taken as x-axis and dissimilarity measures as y-axis. PRx was calculated as cross-correlation coefficient between mean ICP and mean ABP; Mx was calculated as cross-correlation coefficient between mean CBFV and mean CPP.

The study of association between performance of the data-mining based NICP assessment and mean ICP, PRx and Mx indicated a range of mean ICP where the NICP assessment achieved minimal dissimilarity for $e^{(1)}$ and $e^{(5)}$. This region is between 12 and 15 mmHg, which is most populated. Consequently, in certain embodiments, more information is available for data entries having mean ICP within this range that leads to a better performance. PRx generally poses a small but significant negative correlation with the dissimilarity indicating that high correlation between ICP and ABP would lead to better performance of NICP assessment. This can be explained by the fact that ABP is one of input signals for estimating ICP. A better correlation between input and output would then lead to better estimate. On the other hand, Mx shows a small but significant positive correlation with the dissimilarity measure. This behavioral is also expected because CBFV dynamics would reflect ICP dynamics as ICP fluctuations is a feedback input for regulating CBF if pressure autoregulation is intact. Therefore, small Mx indicating a better autoregulation would lead to small dissimilarity measure indicating better NICP assessment.

It has been demonstrated that incorporating measures, e.g., PRx and Mx of autoregulation status in the estimation process can improve the NICP assessment performance. This may explain, at least partially, why Schmidt's method performed in an inferior way to the proposed simulation methods described herein, because the distribution of average Mx of the nine patients in this study was wide ranging from −0.25 to 0.42. Therefore, the database is a mixture of recordings with preserved and impaired autoregulation that would negatively affect the performance of the Schmidt's method. While variations of Schmidt's method can depend on two distinct signal databases separated by autoregulation status for gaining performance, the proposed methods described herein have a flexible structure to select an appropriate database entry on the fly and thus can avoid knowing each patient's autoregulation status as a prior.

Spearman was ρ calculated for each scatter plot for investigating the correlation between x and y variables. Results were reported for scatter plots with significant non-zero ρ ($p < 0.05$). It can be seen from the figure that scatter plot between mean ICP and $e^{(1)}$ has a nonlinear shape with minimal dissimilarity achieved around 15 mmHg. This is the case for $e^{(5)}$ as well. Scatter plot between mean ICP and $e^{(2)}$ has a $$\frac{1}{x}$$

shape because of the mean ICP appears as the denominator in the equation for calculating $e^{(2)}$. Other scatter plots are less regular but some of them showed non-zero cross-correlation. Particularly, it is suggested PRx and dissimilarity has a negative correlation while a positive correlation exists between Mx and dissimilarity.

In certain embodiments, the simulation process of FIG. 5 to assess a patient's ICP does not involve a significant amount of computational cost, and can therefore be processed by a single computer. In certain embodiments, and as compared with the training process of FIG. 1, the simulation process of FIG. 5 involves less computational cost such that the ICP assessment can be performed in a real-time fashion.

In some embodiments, the selection of a particular criterion for optimality, i.e., for determining the optimal dissimilarity from a set of dissimilarity values, can depend on the intended usage of the ICP estimation, or other physiological parameter estimation. For example, one may wish to choose an ICP model with low ICP variability because it is desired to measure, or estimate, subtle drops in ICP over a long period of time, from a fracture of the cranial base. In this case, one may wish to choose an optimal dissimilarity criterion based on low variability.

While certain aspects and embodiments of the invention have been described, these have been presented by way of example only, and are not intended to limit the scope of the invention. Indeed, the novel methods and systems described herein may be embodied in a variety of other forms without departing from the spirit thereof. For example, usage of cerebral blood flow velocity as measured by TCD as described above represents only certain embodiments of the invention.

Other measurement techniques of the above-described ICP-related variables can be integrated with the data-mining framework described above as well. Consequently, certain embodiments of the invention can be considered as a useful data processing technique that can be integrated with other measurement techniques for other clinically important, but difficult physiological or biological signal data and/or variables, due to invasive nature of their measurements. Consequently, other physiological measurements can be used as well within the proposed framework.

For example, certain embodiments of the invention can be used as a data mining framework for dealing with the problem of estimating a desirable time series (DTS) from a set of its related time series (RTS) without the requirement of an explicit prior model relating them. This is made possible by mining a database that consists of instances of DTS and its simultaneously recorded RTS.

Although preferred embodiments of the disclosure have been described in detail, including methods and systems for estimating a value or function of a first physiological parameter, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A system, for determining an estimated intracranial pressure (ICP) of a first patient, comprising:
    a processing module that:
        receives a first input based on a first plurality of measurements of a first physiological parameter of the first patient, the first physiological parameter correlating with ICP;
        receives a second input based on a second plurality of measurements of a second physiological parameter of the first patient, the second physiological parameter correlating with ICP;
        processes the first and second inputs based on an ICP model; and
        outputs data indicative of the estimated ICP of the first patient;
    wherein the ICP model is chosen from a plurality of potential ICP models, each of the potential ICP models corresponding to a respective model patient, other than the first patient, and representing a transform function that transforms (a) time series information indicative of measurements of the first and second physiological parameters of the respective model patient to (b) time series information indicative of measurements of ICP of the respective model patient;
    wherein each of the plurality of models transforms (a) time series information indicative of measurements of the first and second physiological parameters of an index patient other than the respective model patient to (b) time series information indicative of an estimated ICP of the index patient, wherein a dissimilarity value indicates a dissimilarity between the index patient's estimated ICP and the index patient's observed ICP;
    wherein each of the potential ICP models has an associated mapping function that maps values of said first and second physiological parameters, of each patient in a group of patients other than the respective model patient, to at least one dissimilarity value corresponding to each of the patients in the group;
    wherein said ICP model is chosen based on dissimilarity values obtained by applying the mapping functions of each of the potential ICP models to data indicative of the first patient's first and second pluralities of measurements, to determine a dissimilarity value corresponding to each of the potential ICP models.

2. The system of claim 1, wherein a hemodynamic feature vector comprises said values of, or derived values from, said first and second physiological parameters.

3. The system of claim 1, wherein said ICP model is chosen based on dissimilarity values obtained by
    choosing an optimal dissimilarity value from among the corresponding dissimilarity values, based on at least one criterion.

4. The system of claim 3, wherein each of the corresponding dissimilarity values comprises a scalar value.

5. The system of claim 3, wherein a hemodynamic feature vector comprises derived values from said first patient's said first plurality of measurements and second plurality of measurements.

6. The system of claim 3, wherein the at least one criterion comprises determining a minimum dissimilarity value from among the corresponding dissimilarity values.

7. The system of claim 3, wherein the at least one criterion comprises determining the maximum-score dissimilarity value from among the corresponding dissimilarity values.

8. The system of claim 3, wherein the dissimilarity value comprises an expression of a cross correlation coefficient between estimated and observed ICP values or vectors.

9. The system of claim 3, wherein the dissimilarity value comprises an expression of a pulsatile component of at least one of said first plurality of measurements or said second plurality of measurements.

10. The system of claim 3, wherein the dissimilarity value comprises an expression of a slow wave component of at least one of said first plurality of measurements or said second plurality of measurements.

11. The system of claim 1, further comprising an output module that is configured to receive the output produced by the processing module.

12. The system of claim 11, wherein said output module comprises an electronic display.

13. The system of claim 11, wherein said output module comprises a printed display.

14. The system of claim 11, wherein the output module comprises an audible display.

15. The system of claim 1, wherein the processing module comprises computer-executable instructions.

16. The system of claim 1, further comprising a storage module that stores data indicative of at least one of said first plurality of measurements or said second plurality of measurements.

17. The system of claim 1, wherein said output comprises data configured to be stored on a computer-readable medium.

18. The system of claim 1, wherein at least one of said first or second physiological parameters comprises a $pCO_2$.

19. The system of claim 1, wherein at least one of said first or second physiological parameters comprises arterial $pO_2$.

20. The system of claim 1, wherein at least one of said first or second physiological parameters comprises an arterial blood pressure.

21. The system of claim 1, wherein at least one of said first or second physiological parameters is a cerebral blood flow velocity.

22. The system of claim 1, wherein at least one of said first or second physiological parameters comprises an echocardiographic measurement.

23. The system of claim 1, wherein said observed ICP value or function is obtained from a patient other than said first patient.

24. A method, of determining an estimated intracranial pressure (ICP) of a first patient, comprising:
    inputting into an ICP model a first plurality of measurements, of a first physiological parameter of the first patient, the first physiological parameter correlating with ICP;
    inputting into the ICP model a second plurality of measurements, of a second physiological parameter of the first patient, the second physiological parameter correlating with ICP; and outputting from the ICP model the estimated ICP of the patient, wherein the ICP model is chosen from a plurality of potential ICP models, each of the potential ICP models corresponding to a respective model patient, other than the first patient, and representing a transform function that transforms (a) time series information indicative of measurements of the first and second physiological parameters of the respective model patient to (b) time series information indicative of measurements of ICP of the respective model patient;

wherein each of the plurality of models transforms (a) time series information indicative of measurements of the first and second physiological parameters of an index patient other than the respective model patient to (b) time series information indicative of an estimated ICP of the index patient, wherein a dissimilarity value indicates a dissimilarity between the index patient's estimated ICP and the index patient's observed ICP;

wherein each of the potential ICP models has an associated mapping function that maps values of said first and second physiological parameters, of each patient in a group of patients other than the respective model patient, to at least one dissimilarity value corresponding to each of the patients in the group;

wherein said ICP model is chosen based on dissimilarity values obtained by applying the mapping functions of each of the potential ICP models to data indicative of the first patient's first and second pluralities of measurements, to determine a dissimilarity value corresponding to each of the potential ICP models.

25. The method of claim 24, wherein said first plurality of measurements is obtained over time and said second plurality of measurements is obtained over time.

26. The method of claim 24, wherein a hemodynamic feature vector comprises said values of, or derived values from, said first and second physiological parameters.

27. The method of claim 24, further comprising
choosing an optimal dissimilarity value from among the corresponding dissimilarity values, based on at least one criterion.

28. The method of claim 27, wherein a hemodynamic feature vector comprises derived values from said first patient's said first plurality of measurements and second plurality of measurements.

29. The method of claim 27, wherein each of the corresponding dissimilarity values comprises a scalar value.

30. The method of claim 27, wherein the at least one criterion comprises determining a minimum dissimilarity value from among the corresponding dissimilarity values.

31. The method of claim 27, wherein the at least one criterion comprises determining a maximum-score dissimilarity value from among the corresponding dissimilarity values.

32. The method of claim 27, wherein the dissimilarity value comprises an expression of a cross correlation coefficient between estimated and observed ICP values or vectors.

33. The method of claim 27, wherein the dissimilarity value comprises an expression of a pulsatile component of at least one of said first plurality of measurements or said second plurality of measurements.

34. The method of claim 27, wherein the dissimilarity value comprises an expression of a slow wave component of at least one of said first plurality of measurements or said second plurality of measurements.

35. The method of claim 24, wherein at least one of said first or second physiological parameters comprises a $pCO_2$.

36. The method of claim 24, wherein at least one of said first or second physiological parameters comprises an arterial $pO_2$.

37. The method of claim 24, wherein at least one of said first or second physiological parameters comprises an arterial blood pressure.

38. The method of claim 24, wherein at least one of said first or second physiological parameters is a cerebral blood flow velocity.

39. The method of claim 24, wherein at least one of said first or second physiological parameters comprises an echocardiographic measurement.

40. The method of claim 24, wherein said observed ICP value or function is obtained from a patient other than said first patient.

41. The method of claim 24, wherein a signal comprises at least one of said first plurality of measurements or said second plurality of measurements.

42. The method of claim 41, wherein said signal comprises an electrical signal.

43. The system of claim 1, wherein the index patient is one of the model patients.

44. The system of claim 1, wherein each patient in the group is one of the model patients.

45. The method of claim 24, wherein the index patient is one of the model patients.

46. The method of claim 24, wherein each patient in the group is one of the model patients.

* * * * *

UNITED STATES PATENT AND TRADEMARK OFFICE
CERTIFICATE OF CORRECTION

PATENT NO. : 8,821,408 B2  
APPLICATION NO. : 12/296087  
DATED : September 2, 2014  
INVENTOR(S) : Hu et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1591 days.

Signed and Sealed this
Twenty-fifth Day of August, 2015

Michelle K. Lee
*Director of the United States Patent and Trademark Office*